United States Patent
Setia et al.

(10) Patent No.: US 11,894,107 B2
(45) Date of Patent: Feb. 6, 2024

(54) PRECISION-PRESERVING QUBIT REDUCTION BASED ON SPATIAL SYMMETRIES IN FERMIONIC SYSTEMS

(71) Applicant: International Business Machines Corporation, Armonk, NY (US)

(72) Inventors: Kanav Setia, Hanover, NH (US); Sergey Bravyi, Ossining, NY (US); Antonio Mezzacapo, Westchester, NY (US); Richard Chen, Mount Kisco, NY (US); Marco Pistoia, Amawalk, NY (US); Julia Elizabeth Rice, Sunnyvale, CA (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 1142 days.

(21) Appl. No.: 16/660,059

(22) Filed: Oct. 22, 2019

(65) Prior Publication Data
US 2021/0118529 A1      Apr. 22, 2021

(51) Int. Cl.
G01N 33/48        (2006.01)
G01N 33/50        (2006.01)
(Continued)

(52) U.S. Cl.
CPC ............. G16C 10/00 (2019.02); G06F 17/16 (2013.01); G06N 10/00 (2019.01)

(58) Field of Classification Search
CPC .......... G16C 10/00; G06F 17/16; G06N 10/00
See application file for complete search history.

(56) References Cited

U.S. PATENT DOCUMENTS 9,819,347 B2   11/2017   Hastings et al.
10,404,287 B2   9/2019   Haah et al.
(Continued)

FOREIGN PATENT DOCUMENTS

WO      2019070228 A1      4/2019

OTHER PUBLICATIONS

De Avila, et al. "Scalable quantum simulation by reductions and decompositions through the Id-operator." Proceedings of the 31st Annual ACM Symposium on Applied Computing (SAC '16). ACM, New York, NY, USA, 1255-1257. 3 pages.
(Continued)

*Primary Examiner* — Russell S Negin
(74) *Attorney, Agent, or Firm* — Amin, Turocy & Watson, LLP

(57) ABSTRACT

Systems and techniques that facilitate precision-preserving qubit reduction based on spatial symmetries in fermionic systems are provided. In one or more embodiments, a symmetry component can generate a diagonalized second quantization representation of a spatial point group symmetry operation. The spatial point group symmetry operation can be associated with a molecule (e.g., a geometrical rotation, reflection, and/or inversion of a physical molecule that results in a new molecular orientation that is substantially the same as the original molecular orientation). In one or more embodiments, a transformation component can convert the diagonalized second quantization representation into a single Pauli string. In one or more embodiments, a tapering component can taper off qubits in a computational quantum algorithm that models properties of the molecule, based on the single Pauli string. Various embodiments can thus leverage geometrical spatial symmetries of a molecule to reduce a number of qubits needed to simulate the molecule.

20 Claims, 16 Drawing Sheets

(51) Int. Cl.
*G16C 10/00* (2019.01)
*G06N 10/00* (2022.01)
*G06F 17/16* (2006.01)

(56) References Cited

U.S. PATENT DOCUMENTS

2011/0313741 A1* 12/2011 Langhoff ............... G16C 20/30
703/2
2016/0283857 A1 9/2016 Babbush et al.
2019/0228333 A1 7/2019 Bravyi et al.

OTHER PUBLICATIONS

Almeida, et al. "Efficient Realizations of CNOT gates in IBM's Quantum Computers, " 2018 8th International Symposium on Embedded Computing and System Design (ISED), Cochin, India, 2018, pp. 58-62. 5 pages.
Cao, et al. "Quantum Chemistry in the Age of Quantum Computing." arXiv:1812.09976v2 [quant-ph] Dec. 28, 2018. 68 pages.
Dehaene, et al. "The Clifford group, stabilizer states, and linear and quadratic operations over GF(2)." Phys. Rev. A, 68:042318, Oct. 2003. 9 pages.
Kandala, et al. "Hardware-efficient Variational Quantum Eigensolver for Small Molecules and Quantum Magnets." Nature, 549:242-246, 2017. 24 pages.
Kandala, et al. "Error mitigation extends the computational reach of a noisy quantum processor." Nature, vol. 567, Issue 7749, 2019. https://doi.org/10.1038/s41586-019-1040-7. 11 pages.
Kivlichan, et al. "Quantum Simulation of Electronic Structure with Linear Depth and Connectivity." Phys. Rev. Lett., 120:110501, Mar. 2018.
McArdle, et al. "Quantum computational chemistry." arXiv:1808.10402v2 [quant-ph] Jan. 17, 2019. 46 pages.
McArdle, et al. "Error-mitigated digital quantum simulation." Phys. Rev. Lett. 122, 180501 (2019). 17 pages.
Bonet-Monroig, et al. "Low-cost error mitigation by symmetry verification." Phys. Rev. A, 98:062339, Dec. 2018. arXiv:1807.10050v3 [quant-ph] Jan. 2, 2019. 11 pages.
Bravyi, et al. "Tapering off qubits to simulate fermionic Hamiltonians." arXiv:1701.08213v1 [quant-ph] Jan. 27, 2017. 15 pages.
Bravyi, et al. "Fermionic quantum computation." arXiv:quant-ph/0003137v2 Apr. 1, 2000. 18 pages.
Nam, et al. "Ground-state energy estimation of the water molecule on a trapped ion quantum computer." arXiv:1902.10171v2 [quant-ph] Mar. 7, 2019. 14 pages.
Peruzzo, et al. "A variational eigenvalue solver on a photonic quantum processor." Nature Communications, vol. 5, Article No. 4213 (2014). 7 pages.
Setia, et al. "Superfast encodings for fermionic quantum simulation." relarXiv:1810.05274v2 [quant-ph] Dec. 18, 2018. 9 pages.
Temme, et al. "Error mitigation for short-depth quantum circuits." Phys. Rev. Lett. 119, 180509 (2017). arXiv:1612.02058v3 [quant-ph] Nov. 6, 2017. 15 pages.
Berry, et al. "Improved Techniques for Preparing Eigenstates of Fermionic Hamiltonians." Quantum Information 4: 1, 22 (2018). arXiv:1711.10460v3 [quant-ph] Mar. 23, 2018. 16 pages.
Wright, et al. "Benchmarking an 11-qubit quantum computer." arXiv:1903.08181v1 [quant-ph] Mar. 19, 2019. 8 pages.
Cotton. "Chemical Applications of Group Theory" Wiley, 1990. 468 pages.
Preskill. "Quantum Computing in the NISQ era and beyond." arXiv:1801.00862v3 [quant-ph] Jul. 31, 2018. 20 pages.
Wecker, et al. "Gate-count estimates for performing quantum chemistry on small quantum computers." PPhys. Rev. A 90, 022305 (2014).
International search report and written opinion received for PCT aplication No. PCT/EP2020/079685 dated Feb. 3, 2021, 11 pages.
Setia et al., "Reducing Qubit Requirements for Quantum Simulations Using Molecular Point Group Symmetries", Journal of chemical theory and computation, Oct. 31, 2019, 7 pages.
Fischer et al., "Symmetry Configuration Mapping for Compact Representation of Quantum Chemistry on Quantum Computers", arXiv:1907.01493v1 [quant-ph], Jul. 2, 2019, 6 pages.
Steudtner et al., "Lowering qubit requirements for quantum simulations of fermionic systems", arXiv:1712.07067v2 [quant-ph], Oct. 11, 2018, 24 pages.
Yen et al., " Exact and approximate symmetry projectors for the electronic structure problem on a quantum computer", arXiv:1905.08109v2 [quant-ph], Oct. 7, 2019, 13 pages.

* cited by examiner

| | Spin Orbitals $M$ | Jordan-Wigner | Parity | Binary Tree |
|---|---|---|---|---|
| LiH | 12 | $(\sigma_1^x, \sigma_1^z\sigma_2^z\sigma_3^z\sigma_4^z\sigma_5^z\sigma_6^z\sigma_7^z\sigma_8^z\sigma_9^z\sigma_{10}^z\sigma_{11}^z)$ $(\sigma_4^x, \sigma_4^z\sigma_{10}^z)$ $(\sigma_5^x, \sigma_5^z\sigma_{11}^z)$ $(\sigma_7^x, \sigma_7^z\sigma_8^z\sigma_9^z\sigma_{10}^z\sigma_{11}^z)$ | $(\sigma_6^x, \sigma_6^z)$ $(\sigma_3^x, \sigma_3^z\sigma_5^z\sigma_9^z\sigma_{11}^z)$ $(\sigma_4^x, \sigma_4^z\sigma_5^z\sigma_{10}^z\sigma_{11}^z)$ $(\sigma_{12}^x, \sigma_{12}^z)$ | $(\sigma_4^x, \sigma_4^z\sigma_6^z)$ $(\sigma_2^x, \sigma_2^z\sigma_3^z\sigma_6^z\sigma_9^z\sigma_{10}^z)$ $(\sigma_5^x, \sigma_5^z\sigma_{11}^z)$ $(\sigma_8^x, \sigma_8^z\sigma_{12}^z)$ |
| BeH$_2$ | 14 | $(\sigma_1^x, \sigma_1^z\sigma_2^z\sigma_3^z\sigma_4^z\sigma_5^z\sigma_6^z\sigma_7^z\sigma_8^z\sigma_9^z\sigma_{10}^z\sigma_{11}^z\sigma_{12}^z)$ $(\sigma_4^x, \sigma_4^z\sigma_{10}^z\sigma_{11}^z\sigma_{12}^z\sigma_{13}^z\sigma_{14}^z)$ $(\sigma_5^x, \sigma_5^z\sigma_{12}^z)$ | $(\sigma_7^x, \sigma_7^z)$ $(\sigma_3^x, \sigma_3^z\sigma_5^z\sigma_{10}^z\sigma_{12}^z)$ $(\sigma_4^x, \sigma_4^z\sigma_5^z\sigma_{11}^z\sigma_{12}^z)$ $(\sigma_{14}^x, \sigma_{14}^z)$ | $(\sigma_4^x, \sigma_4^z\sigma_6^z\sigma_7^z)$ $(\sigma_2^x, \sigma_2^z\sigma_3^z\sigma_6^z\sigma_{10}^z\sigma_{11}^z)$ $(\sigma_5^x, \sigma_5^z\sigma_{10}^z\sigma_{11}^z\sigma_{12}^z)$ $(\sigma_8^x, \sigma_8^z\sigma_{12}^z\sigma_{14}^z)$ |
| H$_2$O | 14 | $(\sigma_1^x, \sigma_1^z\sigma_2^z\sigma_3^z\sigma_4^z\sigma_5^z\sigma_6^z\sigma_7^z\sigma_8^z\sigma_{11}^z\sigma_{12}^z\sigma_{13}^z\sigma_{14}^z)$ $(\sigma_4^x, \sigma_4^z\sigma_{11}^z)$ | $(\sigma_7^x, \sigma_7^z)$ $(\sigma_{14}^x, \sigma_{14}^z)$ | $(\sigma_4^x, \sigma_4^z\sigma_6^z\sigma_7^z)$ $(\sigma_2^x, \sigma_2^z\sigma_3^z\sigma_6^z\sigma_7^z\sigma_{12}^z\sigma_{14}^z)$ |
| NH$_3$ | 16 | $(\sigma_1^x, \sigma_1^z\sigma_2^z\sigma_3^z\sigma_4^z\sigma_5^z\sigma_6^z\sigma_7^z\sigma_8^z\sigma_9^z\sigma_{10}^z\sigma_{11}^z\sigma_{12}^z\sigma_{13}^z\sigma_{14}^z\sigma_{15}^z\sigma_{16}^z)$ $(\sigma_9^x, \sigma_9^z\sigma_{15}^z\sigma_{16}^z)$ | $(\sigma_8^x, \sigma_8^z)$ $(\sigma_{16}^x, \sigma_{16}^z)$ | $(\sigma_8^x, \sigma_8^z)$ $(\sigma_{16}^x, \sigma_8^z\sigma_{16}^z)$ |
| HCl | 20 | $(\sigma_1^x, \sigma_1^z\sigma_2^z\sigma_3^z\sigma_4^z\sigma_5^z\sigma_6^z\sigma_7^z\sigma_8^z\sigma_9^z\sigma_{10}^z\sigma_{11}^z\sigma_{12}^z\sigma_{13}^z\sigma_{14}^z\sigma_{15}^z\sigma_{16}^z\sigma_{17}^z\sigma_{18}^z\sigma_{19}^z\sigma_{20}^z)$ $(\sigma_{11}^x, \sigma_{11}^z\sigma_{12}^z\sigma_{13}^z\sigma_{14}^z\sigma_{15}^z\sigma_{16}^z\sigma_{17}^z\sigma_{18}^z\sigma_{19}^z\sigma_{20}^z)$ | $(\sigma_{10}^x, \sigma_{10}^z)$ $(\sigma_{20}^x, \sigma_{20}^z)$ $(\sigma_3^x, \sigma_3^z\sigma_5^z\sigma_6^z\sigma_7^z\sigma_{10}^z\sigma_{13}^z\sigma_{15}^z\sigma_{17}^z\sigma_{19}^z)$ $(\sigma_4^x, \sigma_4^z\sigma_5^z\sigma_8^z\sigma_9^z\sigma_{14}^z\sigma_{15}^z\sigma_{18}^z\sigma_{19}^z)$ | $(\sigma_8^x, \sigma_8^z)$ $(\sigma_{16}^x, \sigma_{16}^z)$ $(\sigma_5^x, \sigma_5^z\sigma_9^z\sigma_{15}^z\sigma_{19}^z)$ $(\sigma_{16}^x, \sigma_{16}^z\sigma_{20}^z)$ $(\sigma_2^x, \sigma_2^z\sigma_3^z\sigma_6^z\sigma_7^z\sigma_{10}^z\sigma_{13}^z\sigma_{14}^z\sigma_{17}^z\sigma_{18}^z)$ |

FIG. 2

| Symmetry group | Molecule | qubits req. | qubits tapered | terms before | terms after |
|---|---|---|---|---|---|
| $C_{2v}$ | $H_2O$ | 14 | 4 | 1730 | 966 |
| $C_{3v}$ | $NH_3$ | 16 | 3 | 4577 | 2697 |
| $D_{2h}$ | $C_2H_4$ | 28 | 5 | 30095 | 8919 |
| $D_{3h}$ | $BF_3$ | 40 | 5 | 100885 | 56989 |
| $C_{\infty v}$ | $LiH$ | 12 | 4 | 519 | 519 |
| $D_{\infty h}$ | $H_2$ | 4 | 3 | 27 | 15 |
| | $CO_2$ | 30 | 5 | 20598 | 11302 |
| | $C_2H_2$ | 24 | 5 | 10013 | 5185 |
| | $BeH_2$ | 14 | 5 | 1150 | 666 |
| | $H_2O\,(L)$ | 14 | 5 | 1150 | 666 |

PRECISION-PRESERVING QUBIT REDUCTION BASED ON SPATIAL SYMMETRIES IN FERMIONIC SYSTEMS

BACKGROUND

The subject disclosure relates generally to the optimization of quantum algorithms for computational chemistry simulation, and more specifically to precision-preserving qubit reduction of quantum algorithms based on spatial symmetries in fermionic systems.

SUMMARY

The following presents a summary to provide a basic understanding of one or more embodiments of the invention. This summary is not intended to identify key or critical elements, or delineate any scope of the particular embodiments or any scope of the claims. Its sole purpose is to present concepts in a simplified form as a prelude to the more detailed description that is presented later. In one or more embodiments described herein, devices, systems, computer-implemented methods, apparatus and/or computer program products that facilitate precision-preserving qubit reduction based on spatial symmetries are described.

According to one or more embodiments, a system is provided. The system can comprise a memory that can store computer-executable components. The system can further comprise a processor that can be operably coupled to the memory and that can execute the computer-executable components stored in the memory. In various embodiments, the computer-executable components can comprise a symmetry component, which can generate a diagonalized second quantization representation of a spatial point group symmetry operation. In various embodiments, the spatial point group symmetry operation can be associated with a molecule (e.g., a geometrical rotation, reflection, and/or inversion of the molecule such that the resulting molecular orientation is identical to the original molecular orientation). In various embodiments, the diagonalized second quantization representation can be a diagonal matrix operator, in the second quantized formalism, that corresponds to the application of the spatial point group symmetry operation on vectors representing atomic orbital functions and/or molecular orbital functions of the molecule. In one or more embodiments, the computer-executable components can further comprise a transformation component, which can convert the diagonalized second quantization representation into a single Pauli string (e.g., a tensor product of 2×2 Pauli matrices acting on one or more qubits). In one or more embodiments, the computer-executable components can further comprise a tapering component, which can taper off qubits in a computational quantum algorithm that models properties of the molecule, based on the single Pauli string.

According to one or more embodiments, the above-described system can be implemented as a computer-implemented method. The computer-implemented method can include generating, by a device operatively coupled to a processor, a diagonalized second quantization representation of a spatial point group symmetry operation associated with a molecule. In various embodiments, the computer-implemented method can further comprise converting, by the device, the diagonalized second quantization representation into a single Pauli string. In one or more embodiments, the computer-implemented method can further comprise tapering off, by the device, qubits in a computational quantum algorithm that models properties of the molecule, based on the single Pauli string.

According to one or more embodiments, the above-described system can be implemented as a computer program product for facilitating precision-preserving qubit reduction based on spatial symmetries in fermionic systems. The computer program product can comprise a computer readable storage medium having program instructions embodied therewith. The program instructions can be executable by a processing component, which can cause the processing component to generate a diagonalized second quantization representation of a spatial point group symmetry operation associated with a molecule. In various embodiments, the program instructions can be further executable to cause the processing component to convert the diagonalized second quantization representation into a single Pauli string. In one or more embodiments, the program instructions can be further executable to cause the processing component to taper off qubits in a computational quantum algorithm that models properties of the molecule, based on the single Pauli string.

In various embodiments, the subject claimed innovation can represent spatial symmetries present in a molecule in terms of signed permutation matrices (e.g., the diagonalized second quantization representation) that operate on atomic orbital vectors of the molecule. The second quantized representation of the spatial symmetries can then be transformed using various transformations to obtain a qubit operator form (e.g., a summation of Pauli strings). This qubit operator form can then be used to taper off qubits from a computational quantum algorithm that models properties of the molecule. In other words, various embodiments of the subject claimed innovation can leverage geometrical spatial symmetries present in a molecule to decrease a number of qubits needed to simulate chemical properties and/or chemical interactions of the molecule. This can result in a more optimized use of quantum computing resources during computational simulations of molecules.

DESCRIPTION OF THE DRAWINGS

FIG. 2 illustrates a diagram of example, non-limiting Pauli strings obtained by a qubit tapering-off procedure.

FIG. 11 illustrates a table of example, non-limiting results from precision-preserving qubit reduction based on spatial symmetries in fermionic systems in accordance with one or more embodiments described herein.

DETAILED DESCRIPTION

Figure 1:
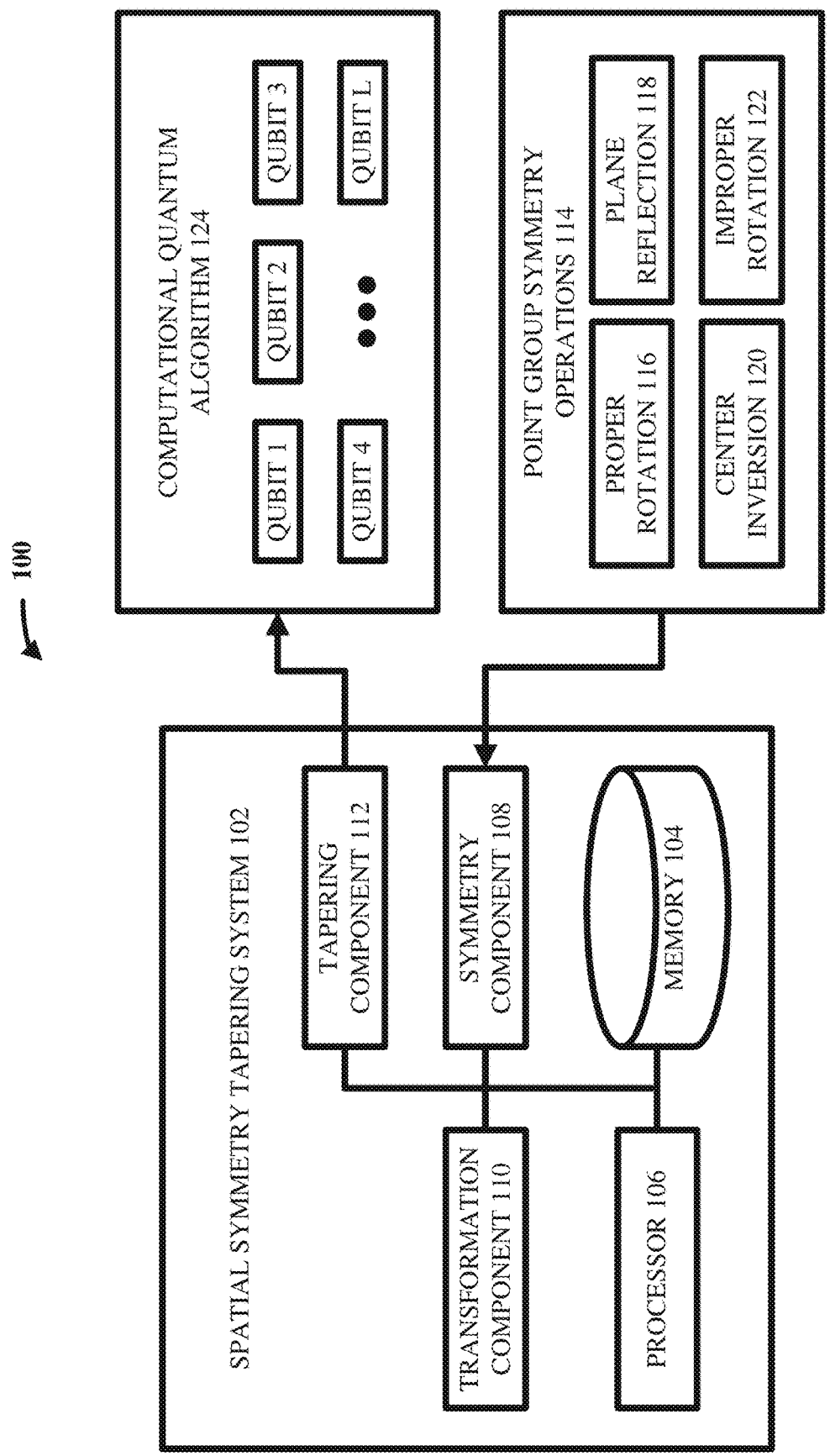
FIG. 1 illustrates a block diagram of an example, non-limiting system that facilitates precision-preserving qubit reduction based on spatial symmetries in fermionic systems in accordance with one or more embodiments described herein.

The following detailed description is merely illustrative and is not intended to limit embodiments and/or application or uses of embodiments. Furthermore, there is no intention to be bound by any expressed or implied information presented in the preceding Background or Summary sections, or in the Detailed Description section.

One or more embodiments are now described with reference to the drawings, wherein like referenced numerals are used to refer to like elements throughout. In the following description, for purposes of explanation, numerous specific details are set forth in order to provide a more thorough understanding of the one or more embodiments. It is evident, however, in various cases, that the one or more embodiments can be practiced without these specific details.

The field of computational chemistry utilizes numerical methods to simulate chemical properties of molecules and/or chemical interactions between molecules. Such numerical approaches are necessary since the quantum many-body problem cannot be satisfactorily addressed in general by analytical methods. To this end, quantum computers (e.g., noisy intermediate-scale quantum (NISQ) devices) and quantum algorithms (e.g., variational quantum eigensolver (VQE)) for simulating chemical properties and/or interactions have the potential to revolutionize the field of computational chemistry. However, current state-of-the-art quantum computing devices are limited in number of qubits, size, coherence, capability, fault tolerance, and so on. These limitations emphasize the importance of continually working to optimize quantum algorithms to conserve computing resources, to execute more efficiently, and to require fewer qubits for accurate simulation.

Various embodiments described herein include systems, computer-implemented methods, apparatus, and/or computer program products that facilitate precision-preserving qubit reduction in computational quantum algorithms based on spatial symmetries in fermionic systems. In other words, one or more embodiments of the subject claimed innovation can leverage geometrical spatial symmetries of a molecule (e.g., rotational symmetries of a physical molecule about an axis, reflectional symmetries of a physical molecule through a plane, inversional symmetries of a physical molecule through a center of inversion, and so on) in order to reduce number of qubits needed to accurately simulate properties and/or interactions of the molecule in a computational quantum algorithm, such as VQE. In one or more embodiments, a spatial point group symmetry operation associated with a molecule can be identified. For example, a water molecule has a rotational point group symmetry operation since an identically-oriented water molecule is obtained by rotating an original water molecule by some amount (e.g., 180°) about its principal axis. Additionally, a water molecule also has a reflectional point group symmetry operation since an identically-oriented water molecule is obtained by reflecting an original water molecule through one of its planes of reflection (e.g., the y-z plane and the x-z plane are both planes of reflection of a water molecule when the z-axis is collinear with the principal axis). In one or more embodiments, a second quantization representation of the spatial point group symmetry operation can be generated. In various embodiments, the second quantization representation can be an operator (e.g., a matrix) which, when multiplied by a vector representing atomic and/or molecular orbitals of the molecule, yields a new vector that corresponds to the atomic and/or molecular orbitals after such orbitals are subjected to the spatial point group symmetry operation. For example, the second quantization representation of a 180° spatial point group symmetry operation of a water molecule can be a matrix which, when multiplied by a vector representing the molecular orbital functions of the water molecule, results in a new vector representing the 180°-rotated molecular orbital functions of the water molecule. In one or more embodiments, the second quantization representation can be diagonalized, as described in detail herein.

In various embodiments, the diagonalized second quantization representation can be converted into a single Pauli string (e.g., a tensor product of 2×2 Pauli matrices) via known fermion-to-qubit transformations (e.g., Jordan-Wigner transformation, Parity transformation, Bravyi-Kitaev transformation, Superfast Encoding transformation, Generalized Superfast Encoding transformation, and so on). In one or more embodiments, the single Pauli string can be used to reduce, via a qubit "tapering off" technique, the number of qubits from a computational quantum algorithm that simulates properties of the molecule without losing computational accuracy or precision. In other words, the number of qubits required to simulate the chemical properties and/or interactions of a molecule can be reduced by leveraging the geometrical spatial symmetries characterizing the molecule.

Various embodiments of the subject innovation can be employed to use hardware and/or software to solve problems that are highly technical in nature (e.g., to facilitate the automated precision-preserving reduction of qubits from a computational quantum algorithm based on spatial symmetries of fermionic systems), that are not abstract and that cannot be performed as a set of mental acts by a human. Further, some of the processes performed can be performed by a specialized computer (e.g., matrix generation, matrix diagonalization, fermion-to-qubit transformation, tapering off of qubits based on Pauli strings, and so on) for carrying out defined tasks related to computational quantum simulation of molecules (e.g., generation of a diagonalized second quantization representation of a spatial point group symmetry associated with a molecule, application of a fermion-to-qubit transformation to yield a single Pauli string, tapering off of qubits based on the single Pauli string, and so on). In various embodiments, the subject claimed innovation can be employed to solve new problems that arise through advancements in technology, computer networks, the Internet, and the like. In various aspects, the subject claimed innovation can provide technical improvements to the field of computational quantum simulation of chemistry, by leveraging geometric spatial symmetries present in a molecule to reduce the number of qubits required to accurately simulate the molecule. By generating a particular diagonalized second quantization representation of the spatial symmetry, the subject claimed innovation can convert the diagonalized second quantization representation into a single Pauli string and apply a qubit "tapering off" methodology based on the single Pauli string to reduce the number of qubits needed to simulate the molecule without any commensurate drop in simulation accuracy, precision, or efficacy. Such precision-preserving reduction of qubits based on spatial symmetries of fermionic systems can result in further qubit reduction than the qubit "tapering off" method alone, and thus constitutes a concrete and tangible technical improvement in the prior art.

FIG. 1 illustrates a block diagram of an example, non-limiting system 100 that can facilitate precision-preserving qubit reduction based on spatial symmetries in fermionic systems in accordance with one or more embodiments described herein. As shown, a spatial symmetry tapering system 102 can leverage one or more point group symmetry operations 114 associated with a given molecule in order to reduce a number of qubits needed in a computational quantum algorithm 124 to model chemical properties and/or chemical interactions of the molecule.

In various instances, the point group symmetry operations 114 can be described in terms of symmetry operations and/or symmetry elements. A symmetry operation can be a physical movement of a body (e.g., a molecule) such that, after the movement, every point of the body coincides with an equivalent or same point of the body in the original configuration. A symmetry element can be a geometrical entity (e.g., a line, a plane, a point, and so on) with respect to which one or more symmetry operations can be carried out. In other words, the point group symmetry operations 114 can, in various embodiments, include one or more geometrical rotations of a given molecule about an axis/line, one or more geometrical reflections of the molecule through a plane, one or more geometrical inversions of the molecule through a point, and/or any combination of operations thereof that do not change the orientation of the molecule (e.g., such that the resulting molecular orientation after the symmetry operation is identical to the original molecular orientation before the symmetry operation).

Figure 9:
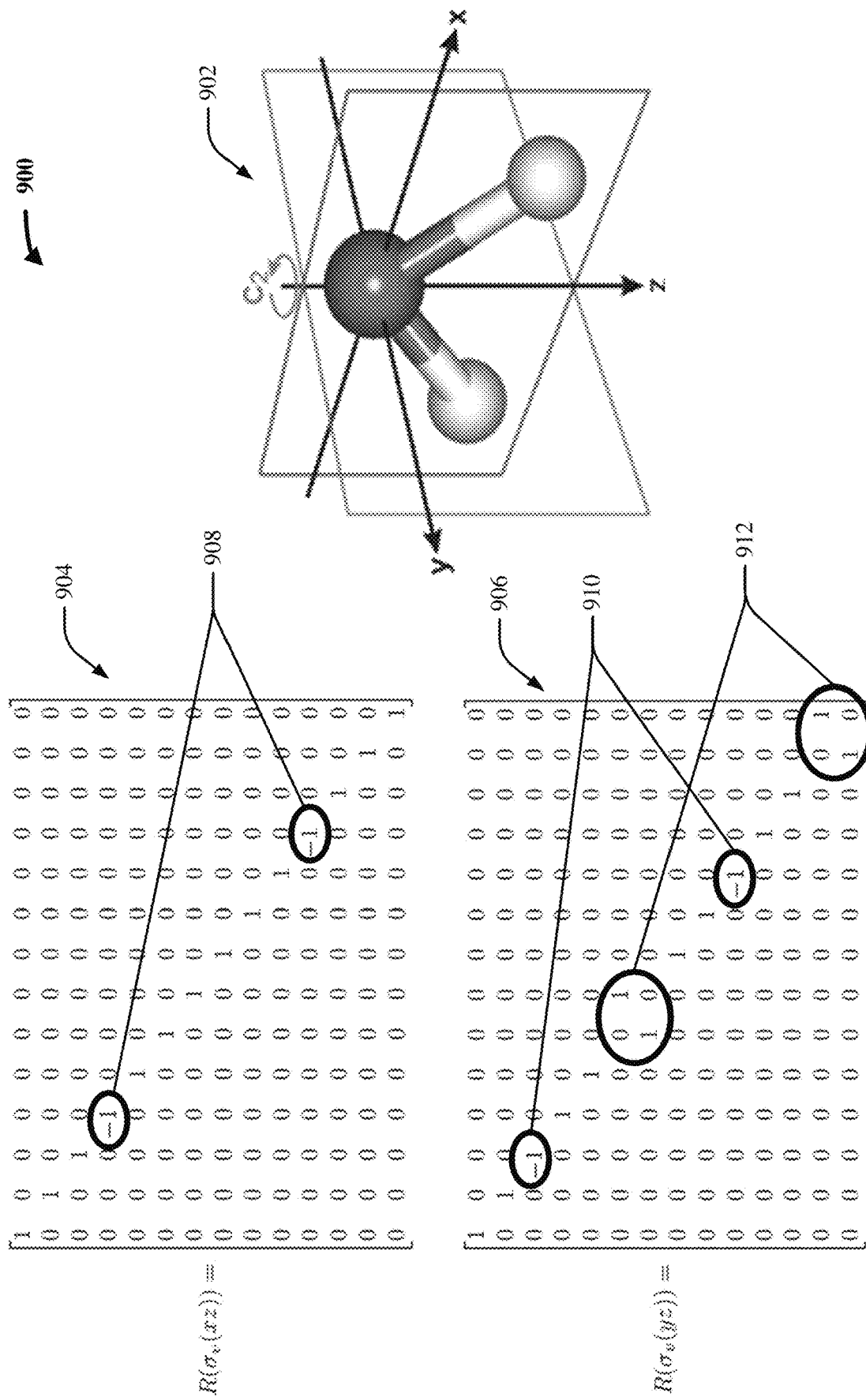
FIG. 9 illustrates a diagram of example, non-limiting matrices representing spatial point group symmetry operations of a water molecule that can be used to facilitate precision-preserving qubit reduction based on spatial symmetries in fermionic systems in accordance with one or more embodiments described herein.

In one or more embodiments, the point group symmetry operations 114 can include a proper rotation 116, a plane reflection 118, a center inversion 120, and/or an improper rotation 122. In various aspects, a proper rotation 116 can be a rotation $C_n$ of $(360/n)°$ about a principal axis of a molecule. For example, a water molecule has a $C_2$ proper rotational symmetry since a 180° (e.g., $(360/2)°=180°$ rotation of the water molecule about its principal axis (e.g., the axis that passes through the oxygen atom, that is coplanar with the two hydrogen atoms, and that bisects the H—O—H bond angle, as shown in FIG. 9) yields an identically-oriented water molecule (e.g., the hydrogen atoms simply switch places and the $2p_x$ and $2p_y$ orbitals of the oxygen atom pick up a phase). In various aspects, a plane reflection 118 can be a reflection a through a plane of symmetry of the molecule. For example, a water molecule has a $\sigma_{yz}$ reflectional symmetry since a reflection through the y-z plane (e.g., the plane that contains the oxygen atom, that does not contain the hydrogen atoms, and that bisects the H—O—H bond angle when the principal axis is collinear with the z-axis, as shown in FIG. 9) yields an identically-oriented water molecule (e.g., the hydrogen atoms simply switch places and the $2p_x$ orbitals pick up a phase). As another example, a water molecule also has a $\sigma_{xz}$ reflectional symmetry since a reflection through the x-z plane (the plane that contains both hydrogen atoms and the oxygen atom when the principal axis is collinear with the z-axis, as shown in FIG. 9) also yields an identically oriented water molecule (e.g., the $2p_y$ orbitals simply pick up a phase). In various aspects, a center inversion 120 can be a diametric opposition/inversion of a molecule through a center of symmetry (e.g., transforming the point (x, y, z) in Euclidean space to (−x, −y, −z) if the origin is the center of symmetry). For example, an ethylene molecule has a center of inversion (e.g., the point directly between the two carbon atoms) such that diametric opposition through this center yields an identically oriented ethylene molecule (e.g., the two carbon atoms switch places, and each hydrogen atom switches places with its diagonally opposite hydrogen atom). In various aspects, an improper rotation 122 can be a rotation $S_n$ of $(360/n)°$ about the principal axis of a molecule followed by a reflection through a plane orthogonal to the principal axis. It can be shown that an $S_2$ improper rotation can be equivalent to a center inversion and that a reflection through a plane normal to the principal axis can be equivalent to an $S_1$ improper rotation.

It is to be appreciated that the point group symmetry operations 114 for any given molecule can constitute a mathematical group (e.g., a set that satisfies the canonical group axioms of closure, associativity, identity, and invertibility). Since each symmetry operation leaves at least one point of a molecule unchanged, the group is referred to as point group symmetries.

Although FIG. 1 depicts the point group symmetry operations 114 as comprising exactly four symmetry operations, this is for non-limiting, illustrative purposes only. It will be appreciated that different molecules can have different and/or any number and/or any type and/or any combination of point group symmetry operations 114, based on the geometry of the molecule. Indeed, molecules belong to different point groups based on the different symmetry elements that leave the molecule unchanged. For example, water ($H_2O$) belongs to the point group $C_{2v}$ since water has a vertical proper rotation axis $C_2$ (e.g., a 180° rotation) and at least one vertical plane of reflection. As another example, ammonia ($NH_3$) belongs to the point group $C_{3v}$ since it has a vertical proper rotation axis $C_3$ (e.g., a 120° rotation) and at least one vertical plane of reflection. In various instances, different molecules can belong to different point groups, and such point groups can be represented by character tables. For instance, an exemplary character table of $C_{3v}$ is given below.

| $C_{3v}$ | E | $2C_3$ | $3\sigma_v$ |
|---|---|---|---|
| $A_1$ | 1 | 1 | 1 |
| $A_2$ | 1 | 1 | -1 |
| E | 2 | -1 | 0 |

Entries in the table can be the characters of symmetry operations within different irreducible representations. For each irreducible representation (e.g., irrep), the trace of the matrix representing that irrep can be called the character. The labels for each row can correspond to different irreps, and the symmetry elements can be grouped into classes matching each column.

In one or more embodiments, the computational quantum algorithm 124 can be any quantum device and/or quantum algorithm that contains and/or makes use of one or more qubits to simulate and/or approximate chemical properties and/or chemical interactions (e.g., energy eigenstates, and so on) of one or more molecules, such as variational quantum eigensolver. In various embodiments, the computational quantum algorithm 124 can comprise any quantum device and/or algorithm for simulating quantum chemistry that is now known or later developed. As shown, the computational quantum algorithm 124 can, in various embodiments, contain and/or make use of one or more qubits (e.g., qubit 1, qubit 2, qubit 3, qubit 4, . . . , qubit L) in simulating chemical properties and/or interactions of a given molecule. In various aspects, L in this context can be any suitable number and can depend on the complexity of the molecule to be simulated (e.g., the simulation of geometrically complicated molecules can require more qubits than the simulation of geometrically simple molecules).

In order to preserve computing resources and improve computing efficiency, it is advantageous to reduce the number of qubits required by the computational quantum algorithm 124 to simulate the given molecule without any commensurate decrease in simulation accuracy and/or precision. As mentioned above and as described in more detail below, in various embodiments, the spatial symmetry tapering system 102 can achieve this precision-preserving reduction of qubits in the computational quantum algorithm 124 by leveraging the point group symmetry operations 114.

In various embodiments, the spatial symmetry tapering system 102 can comprise a processor 106 (e.g., computer processing unit, microprocessor, and so on) and a computer-readable memory 104 that is operably and/or operatively and/or communicatively connected/coupled to the processor 106. The memory 104 can store computer-executable instructions which, upon execution by the processor 106, can cause the processor 106 and/or other components of the spatial symmetry tapering system 102 (e.g., symmetry component 108, transformation component 110, tapering component 112, and so on) to perform one or more acts. In various embodiments, the memory 104 can store computer-executable components (e.g., symmetry component 108, transformation component 110, tapering component 112, and so on), and the processor 106 can execute the computer-executable components.

In some aspects, the spatial symmetry tapering system 102 can, via a symmetry component 108, generate a second quantization representation of one or more of the point group symmetry operations 114. In various embodiments, the second quantization representation can be a matrix operator in the second quantization basis that corresponds to one or more of the point group symmetry operations 114. In various cases, there are various ways of representing the point group symmetry operations 114 as matrices in different bases. For example, consider a point $\vec{r}^{\,2}=[x, y, z]$ in space (e.g., three-dimensional Euclidean space). For a 180° proper rotational symmetry in the point group symmetry operations 114, a 3×3 matrix A can be generated and/or obtained that represents and/or corresponds to the 180° rotation about the principal axis. In such case, the matrix A can be multiplied by the vector $\vec{r}^{\,2}$ to yield the rotated vector $\vec{r}'$, where $\vec{r}'$ represents the resultant vector after the original vector $\vec{r}$ is transformed. That is, $\vec{r}'=A\vec{r}$, meaning that $\vec{r}'$ is the vector obtained after $\vec{r}$ is rotated about its principal axis by 180°. For instance, the following matrices represent exemplary matrix representations, in the standard basis of three-dimensional Euclidean space, of various exemplary point group symmetry operations:

$$\sigma_{xy} = \begin{bmatrix} 1 & 0 & 0 \\ 0 & 1 & 0 \\ 0 & 0 & -1 \end{bmatrix}$$

$$\sigma_{xz} = \begin{bmatrix} 1 & 0 & 0 \\ 0 & -1 & 0 \\ 0 & 0 & 1 \end{bmatrix}$$

$$\sigma_{yz} = \begin{bmatrix} -1 & 0 & 0 \\ 0 & 1 & 0 \\ 0 & 0 & 1 \end{bmatrix}$$

$$C_n = \begin{bmatrix} \cos\phi & \sin\phi & 0 \\ -\sin\phi & \cos\phi & 0 \\ 0 & 0 & 1 \end{bmatrix} \text{ where } \phi = \frac{2\pi}{n}$$

The above-pictured $\sigma_{xy}$ is a 3×3 matrix that represents a reflection through the x-y plane. If a vector in three-dimensional Euclidean space is multiplied by this $\sigma_{xy}$ matrix, the original x-coordinate and the original y-coordinate of the vector remain unchanged, while the z-coordinate flips signs. Similarly, the above-pictured $\sigma_{xz}$ is a 3×3 matrix that represents a reflection through the x-z plane (e.g., the x-coordinate and z-coordinate remain unchanged while the y-coordinate flips signs). Likewise, the above-pictured $\sigma_{yz}$ is a 3×3 matrix that represents a reflection through the y-z plane (e.g., the y-coordinate and the z-coordinate remain unchanged while the x-coordinate flips signs). Moreover, the above-pictured $C_n$ is a 3×3 matrix that represents a clockwise rotation of $\phi$ radians about the z-axis (e.g., the z-coordinate remains unchanged while the x-coordinate and y-coordinate are multiplied by the shown trigonometric functions consistent with a clockwise rotation). The above matrices are exemplary only, and, in various aspects, any point group symmetry operation can be represented as a matrix operator acting on a three-dimensional Euclidean vector. In various embodiments, any suitable mathematical and/or geometrical techniques now known or later developed can be used to generate such matrices.

In one or more embodiments, point group symmetry operations 114 can also and/or instead be represented by matrices in different bases (e.g., in a basis set different from the standard basis in three-dimensional Euclidean space). For instance, a matrix corresponding to one or more of the point group symmetry operations 114 can be written in the basis of atomic and/or molecular orbital functions (e.g., Gaussian-type orbitals, Slater-type orbitals, numerical atomic orbitals, and so on). In various instances, minimal basis sets can be used, such as STO-nG, STO-3G, STO-6G, cc-pVDZ, cc-pVTZ, and/or any other suitable basis set now known or later developed. In various aspects, symmetry adapted linear combinations (SLACs) can be built by considering a vector representation of atomic orbital functions and/or molecular orbital functions and by building matrices that transform these orbital vectors according to the point group symmetry operations 114, in much the same way the above-described three-dimensional Euclidean matrices transform three-dimensional Euclidean vectors. In other words, while a matrix in three-dimensional Euclidean space can act on and/or transform a vector that represents a linear combination of the basis position vectors (e.g., $\vec{i}, \vec{j}, \vec{k}$), a matrix in the basis of atomic and/or molecular orbitals can act on and/or transform a vector that represents a linear combination of atomic and/or molecular orbital functions. As explained more thoroughly below, such a matrix can be said to be in the second quantization formalism. In one or more embodiments, a matrix in the second quantization formalism can operate on a vector of creation and/or annihilation operators. For a system with n fermionic modes (e.g., n spin orbitals), an n-dimensional orbital vector can represent the state of the fermionic system, and an n-by-n matrix can correspond to the application of one or more spatial symmetry operations on the fermionic system in the basis of atomic and/or molecular orbitals. For example, consider a hydrogen molecule ($H_2$). Such a molecule can have four fermionic modes. If a single is orbital is placed on each hydrogen atom, a $C_2$ rotation and a $\sigma_{yz}$ reflection of the hydrogen molecule will each have the net effect of swapping the two hydrogen atoms. In the STO-3G minimal basis set, these transformations can be represented as a 4×4 matrix operator as shown below:

$$C_2 = \sigma_{yz} = \begin{bmatrix} 0 & 1 & 0 & 0 \\ 1 & 0 & 0 & 0 \\ 0 & 0 & 0 & 1 \\ 0 & 0 & 1 & 0 \end{bmatrix}$$

The matrix above can operate to switch the first and second orbital functions (e.g., as shown by the top two rows of the matrix) and can operate to switch the third and fourth orbital functions (e.g., as shown by the bottom two rows of the matrix) of an original orbital vector of the hydrogen molecule. Such a transformation of an atomic orbital functions vector of a hydrogen molecule can, in various embodiments, be consistent with a 180° rotation about the z-axis and/or a reflection through the y-z plane.

The above matrix is exemplary only and that any point group symmetry operation can be represented as an n-by-n matrix operator acting on an n-dimensional atomic orbital function vector. In various embodiments, any suitable mathematical and/or geometrical techniques now known or later developed can be used to generate such matrices.

In various aspects, the symmetry component 108 can diagonalize the second quantization representation of the one or more point group symmetry operations 114, thereby yielding a diagonalized second quantization representation (e.g., a diagonalized n-by-n matrix that can operate on n-dimensional atomic orbital function vectors). As described more thoroughly below, one or more embodiments of the subject claimed innovation can include a particular diagonalization process that allows the second quantization representation to be converted into a single Pauli string and to thus be able to facilitate tapering off of qubits from the computational quantum algorithm 124.

In one or more embodiments, the spatial symmetry tapering system 102 can, via a transformation component 110, convert the diagonalized second quantization representation of the one or more point group symmetry operations 114 into a single Pauli string. In various aspects, the transformation component 110 can achieve such conversion by employing any fermion-to-qubit mapping now known or later developed (e.g., Jordan-Wigner transformation, Parity transformation, Bravyi-Kitaev transformation, Superfast Encoding transformation, Generalized Superfast Encoding transformation, and so on).

In various embodiments, the spatial symmetry tapering system 102 can, via a tapering component 112, taper off one or more qubits from the computational quantum algorithm 124, based on the single Pauli string generated by the transformation component 110. A description of the tapering-off technique is provided below to help clarify the subject claimed innovation.

At a high level, the tapering-off procedure can involve finding one or more Pauli strings (e.g., a tensor product of any number of 2×2 Pauli matrices) for a given molecule, such that the Pauli strings commute with the Hamiltonian of the molecule. Such Pauli strings/operators can be called the symmetries of the Hamiltonian. Based on these Pauli strings, a unitary matrix operator can be found which transforms the Hamiltonian in such a way that the Hamiltonian acts trivially (e.g., with the identity) on a set of qubits or acts at most with a single Pauli gate/matrix on the set of qubits. The four 2×2 Pauli matrices are shown below:

$$\sigma_0 = \begin{bmatrix} 1 & 0 \\ 0 & 1 \end{bmatrix}; \sigma_x = \begin{bmatrix} 0 & 1 \\ 1 & 0 \end{bmatrix}; \sigma_y = \begin{bmatrix} 0 & -i \\ i & 0 \end{bmatrix}; \sigma_z = \begin{bmatrix} 1 & 0 \\ 0 & -1 \end{bmatrix}$$

In various instances, the qubits on which the transformed Hamiltonian acts trivially or at most with a single Pauli gate can be left out of the simulation (e.g., those qubits can be "tapered off"). Note that the tapering-off method works only with single Pauli strings (e.g., tensor products of one of the four 2×2 Pauli gates with itself on one or more qubits); if the Pauli string is not a single Pauli string, the tapering-off procedure does not identify it. A more detailed explanation of the tapering-off technique follows.

A system with M fermionic modes can be described by the following Hamiltonian in second quantization formalism:

$$H = \sum_{ij}^{M} h_{ij} a_i^\dagger a_j + \frac{1}{2} \sum_{ijkl}^{M} h_{ijkl} a_i^\dagger a_j^\dagger a_k a_l$$

where $h_{ij}$ and $k_{ijkl}$ are the respective one-body and two-body integrals (which can be obtained for a given molecule from various quantum chemistry software packages), and where $\{a'_i, a'_j, \ldots\}$ and $\{a_i, a_j, \ldots\}$ are the respective creation and annihilation operators which obey the canonical commutation relations:

$$a_i a_j + a_j a_i = 0; \; a_i a_j^\dagger + a_j^\dagger a_i = \delta_{ij} I$$

A fermion-to-qubit transformation can then be used to map the second quantization Hamiltonian to qubit operators (e.g., Jordan-Wigner, Parity, Bravyi-Kitaev, Superfast Encoding, Generalized Superfast Encoding, and so on). The transformed Hamiltonian (denoted H) can be a summation of Pauli gates, which takes the following form:

$$H = \Sigma c_j \eta_j$$

where $\eta_j$ are strings of single-qubit Pauli gates (e.g., tensor products of one or more of the 2×2 Pauli matrices). For Jordan-Wigner, Parity, and Bravyi-Kitaev transformations, the length of the string can be M (e.g., the same as the number of modes). For other mappings (e.g., Superfast Encoding, Generalized Superfast Encoding, and so on), a different length is possible.

In various aspects, $\eta_j \in \mathcal{P}_M$, where $\mathcal{P}_M$ is a Pauli group given by:

$$\mathcal{P}_M = \pm \{\sigma_0, \sigma_x, \sigma_y, \sigma_z\}^{\otimes M}$$

Consider a set of k qubits out of a total of M, on which the terms $\eta_j$ in the transformed Hamiltonian act trivially (e.g., with the identity operator). In such case, those k qubits do not need to be included in the simulation. In various aspects, those k qubits can still be left out of the simulation if all the terms $\eta_j$ act on the k qubits with at most one Pauli gate (e.g., $\sigma_x$). In various cases, the single-qubit Pauli gates appearing in various $\eta_j$ terms can be replaced by their eigenvalues (e.g., the eigenvalues of all the 2×2 Pauli matrices are ±1), and their corresponding qubits can be left out of the simulation (e.g., tapered off).

To place the Hamiltonian in a form that acts trivially or at most with one Pauli gate on a set of k qubits, consider an abelian group $S \in \mathcal{P}_m$, such that $-I \notin S$. Such a group is called a symmetry of the Hamiltonian if all the elements of S commute with each Pauli term of the Hamiltonian.

Let $\{\tau_1, \tau_2, \ldots, \tau_k\}$ be the set of generators of the symmetry group S. From stabilizer theory, it is known that:

$$U_i \tau_i U_i^\dagger = \sigma_x^{q(i)}; \; q = \{p, q \ldots, s\}$$

where $U_i \in \mathcal{C}_M$, where $\mathcal{C}_M$ is the Clifford Group. The Clifford Group, $\mathcal{C}_M$, on M qubits can be defined as the set of unitary operators, U, such that:

$$U\gamma U \in \mathcal{P}_M; \; \forall \gamma \in \mathcal{P}_M$$

These unitary operators U, once found, can be used to transform the generator set of the symmetry group S to single-qubit Pauli operators (as shown above). Transforming the qubit-operator form of the Hamiltonian, H, by the same unitary operators ensures that the newly transformed Hamiltonian, commutes with the single-qubit Pauli operator, $\sigma_x^{q(i)}$. That is:

$$U_i H U_i^\dagger = \Sigma c_j \sigma_j \text{ and } [\sigma_j, \sigma_x^{q(i)}] = 0$$

where $\sigma_j = U_i \eta_j U_i^\dagger$. This implies that the transformed Hamiltonian, $U_i H U_i^\dagger$, acts trivially or at most with $\sigma_x$ (e.g., a single Pauli gate) on the q(i)$^{th}$ qubit. This allows the $\sigma_x$ on the q(i)$^{th}$ qubit to be replaced with the eigenvalue (e.g., ±1), and so the q(i)$^{th}$ qubit can be left out of the simulation.

Now, consider how to determine the symmetry group S and its generator set. A Pauli string, $\eta$, acting on N qubits can be parameterized by a binary string $(a_x | a_z)$, of length 2N where each component of vectors $a_x$ and $a_z$ are zero or one (e.g., $\{a_x, a_z\} \in \{0,1\}^{\otimes N}$). Qiskit uses the same representation for the Pauli class to represent a Pauli string. This way each $\eta(a_x | a_z)$ can be represented as:

$$\eta(a_x | a_Z) = \prod_{i \in a_x} \sigma_x^i \cdot \prod_{j \in a_z} \sigma_z^j$$

This parameterization is very effective to multiply two Pauli strings, or to check whether the terms commute:

$$\eta(a_x | a_z) \eta(b_x | b_z) = (-1)^{a_x b_z + a_z b_x} \eta(b_x | b_z) \eta(a_x | a_z)$$

In order for the terms to commute, $a_x b_z + a_z b_x = 0 \mod 2$. Now, all the Pauli strings appearing in the Hamiltonian can be represented by a binary matrix:

$$G(H) = \begin{bmatrix} G_x \\ G_z \end{bmatrix}$$

where the j$^{th}$ column of G is a binary matrix corresponding to $(a_x | a_z)$ representing $\eta_j$. It can be seen that the size of the G matrix will be 2Mr, where r is the total number of terms in the Hamiltonian. From the G matrix, another check matrix, E, can be constructed:

$$E = [(G_z)^T | (G_x)^T]$$

It can be observed that the kernel of the check matrix, E, gives the elements of the symmetry group S. Using the Ker(E), one can obtain the generators, $\tau_i$, of the group S by using the Gram-Schmidt orthogonalization procedure over the binary field, $Z_2$.

Now, consider how to determine the unitary operators U. Once the generators of the symmetries $\{\tau_i \in \mathcal{S}\}$ of the Hamiltonian are obtained, then as discussed above, each of these) symmetries can be turned into a Pauli-X operator on a single qubit (e.g., $U_i \tau_i U_i^\dagger = \sigma_x^{q(i)}$). To find the unitary, U, find the $\sigma_x$ on a qubit such that it anti-commutes with one of the symmetries (e.g., $\tau_i$) and commutes with all the other symmetries (e.g., the remaining $\tau_j \in \mathcal{S}$ where $j \neq i$). Then, $$U_i = \frac{1}{\sqrt{2}} (\tau_i + \sigma_x^{q(i)})$$

Further, permutation operators, W, can be used to bring qubits belonging to the set q to the end (and/or beginning, as desired) of the total set of qubits. Different permutation matrices W can be selected to achieve the rearrangement of qubits desired. These $U_i$s along with permutation operators $W_i$s can then be used to transform the Hamiltonian, as shown:

$$(U_1 W_1 U_2 W_2 \ldots U_k W_k) H (W_k^\dagger U_k^\dagger \ldots W_1^\dagger U_1^\dagger) = \Sigma c_j \sigma_j$$

where $W_i$s are the permutation matrices. The transformed Hamiltonian now commutes with $\sigma_x^{q(i)}$. This implies that all the terms in the Hamiltonian must act trivially on the last (and/or first, as the case may be) k-qubits or with just $\sigma_x$'s. In the case of variational quantum eigensolver algorithm, the last k qubits can be left out (e.g., tapered off) and the corresponding $\sigma_x$ operators can be replaced with their eigenvalues, ±1.

The foregoing explanation of tapering-off qubits is non-limiting and illustrative only.

FIG. 2 illustrates a diagram of example, non-limiting Pauli strings obtained by a qubit tapering-off procedure.

As shown, FIG. 2 depicts a table 200 that lists exemplary symmetries (e.g., Pauli strings) derived from various fermion-to-qubit transformations (e.g., Jordan-Wigner, Parity, Binary Tree, and so on) for various exemplary molecules (e.g., LiH, BeH$_2$, H$_2$O, NH$_3$, HCl, and so on). The listed Pauli strings were generated during the above-described tapering-off procedure, meaning that the listed strings represent obtained symmetries of the Hamiltonian for the shown molecules. During the tapering-off procedure, the STO-3G basis set was used, the molecular Hamiltonian was represented in an atomic orbital basis, and Pyquante was used to get the one-body and two-body integrals. As shown, all the obtained symmetries can be represented as single Pauli strings.

For some of the obtained symmetries, the corresponding physical meaning was clear (e.g., if the Jordan-Wigner transform was used, the string $Z^{\otimes N}$ corresponds to the parity of the fermions). For instance, the Pauli string 202 corresponds to the spin-up electrons being conserved in the lithium hydride molecule. However, for other listed Pauli strings (e.g., symmetries of the Hamiltonian), the corresponding physical significance was not clear or understood. For instance, the physical meanings of the Pauli strings 204 were not known to those having ordinary skill in the art prior to the subject claimed innovation.

The inventors of the subject claimed innovation were the first to recognize the physical significance of these less-understood symmetries; that these less-understood symmetries of the Hamiltonian correspond to the geometric symmetries of the physical molecule. Moreover, the inventors of the subject claimed innovation were the first realize that, because the tapering-off qubit procedure generates only single Pauli strings, it is possible, in various cases, that there exist other symmetries of the Hamiltonian for any given molecule that are not single Pauli strings and thus would not show up in the tapering-off procedure. In various embodiments, the subject claimed innovation can leverage the geometric symmetries of a molecule (e.g., the point group symmetry operations 114) to generate such symmetries of the Hamiltonian that would not show up in the normal tapering-off procedure (e.g., symmetries that are not single Pauli strings). As described herein, various embodiments of the subject claimed innovation can manipulate these symmetries into single Pauli representations that can then be used to taper off additional qubits (e.g., at least one more qubit) than the normal tapering-off procedure alone.

Figure 3:
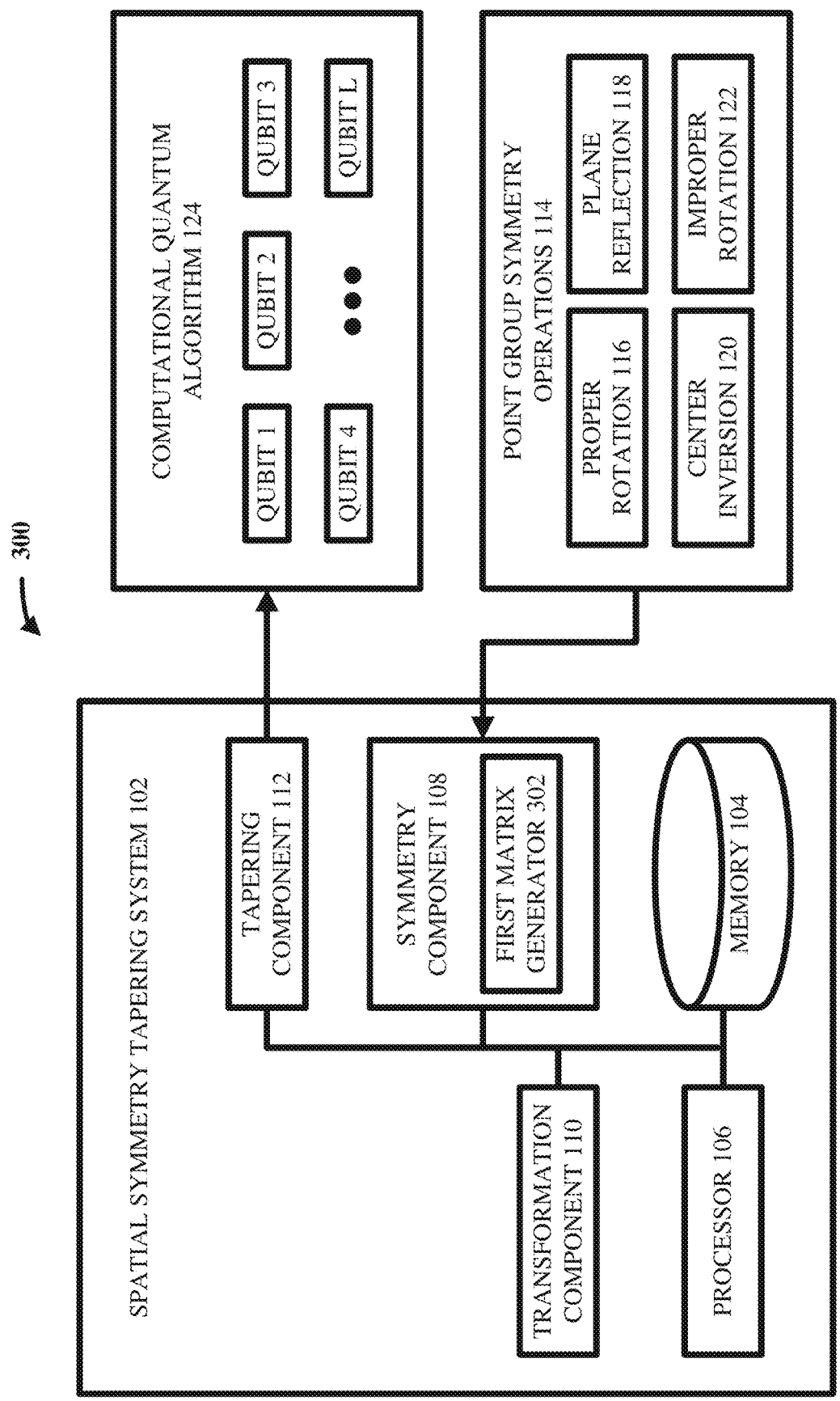
FIG. 3 illustrates a block diagram of an example, non-limiting system including a first matrix generator that facilitates precision-preserving qubit reduction based on spatial symmetries in fermionic systems in accordance with one or more embodiments described herein.

FIG. 3 illustrates a block diagram of an example, non-limiting system 300 including a first matrix generator that can facilitate precision-preserving qubit reduction based on spatial symmetries in fermionic systems in accordance with one or more embodiments described herein. As shown, in one or more embodiments, the system 300 can comprise the same components as the system 100, and can further comprise a first matrix generator 302.

In various instances, the first matrix generator 302 can generate a second quantization representation (e.g., a matrix in second quantized formalism) that can correspond to one or more of the point group symmetry operations 114. As explained herein, such a representation can be used to taper off qubits.

Consider a finite set of single particle wave functions of a molecule given by $$\{\phi_i(x), i \in [1, M]\}.$$

The basis set becomes complete as $M \to \infty$. As it is computationally expensive to deal with large basis sets, truncated basis sets can be used. Now, assume the system under consideration has some point group symmetry operation. If R is the operator that defines this point group symmetry operation, then:

$$\phi'_i(x) = R(\phi_i(x))$$

If the basis set is complete, the new basis functions, $\phi'_i(x)$, can always be represented as a linear combination of the older basis functions, $\phi_i(x)$. Even with truncated basis sets, it is possible to pick the truncated basis set in such a way that R ends up being a linear transformation which gives:

$$\varphi_i(x) = \Sigma R_{ji} \phi_j(x)$$

Further, it is preferable to make R a unitary matrix so that the new basis set spans the same space as the old basis set and so that the transformed second quantization operators still satisfy the canonical commutation relations. In second quantization formalism, the R matrix can be given by:

$$b_i = \sum_{j=1}^{M} R_{ji} a_j$$

where, $b_i$ and $a_j$ are the second quantization operators associated with $\varphi_i(x)$ and $\phi_j(x)$, respectively. For a given molecule, there exists an M×M matrix representation for each symmetry operation, R. The matrices will then follow the multiplication table.

The one-body integrals, $\{h_{ij}\}$, can be represented by an M×M matrix and the two-body integrals, $\{h_{ijkl}\}$, can be represented by an M×M×M×M matrix. In various aspects, the unitary matrix R can be used to transform the one-body and two-body matrices and check whether the Hamiltonian remains the same. This can be the same as checking the commutator of the Hamiltonian with the symmetry. The commutation of the R matrix with the Hamiltonian verifies that it is a symmetry.

Note that, in various embodiments, it is possible to check the commutation of the R matrix with the Hamiltonian without going to the $2^M \times 2^M$ representation of the Hamiltonian. In various instances, any fermion-to-qubit transformation can be used to come up with a qubit operator representation of the R matrix. In general, the qubit representation of the R matrix can end up being a summation of Pauli strings. The tapering-off procedure discussed above can be used if the symmetry is a single Pauli string. Various portions of the herein disclosure teach how to ensure that the qubit representation of the R matrix is a single Pauli string.

In one or more embodiments, a symmetry of the second quantized Hamiltonian for a given molecule can be represented by a signed permutation matrix (e.g., R can be a signed permutation matrix for a given point group symmetry operation of a given molecule when a suitable basis set is chosen to represent the orbitals of the molecule). In various instances, it is possible to pick a basis set such that R is a unitary signed permutation matrix. In various embodiments, non-limiting examples of suitable basis sets can include STO-3G, STO-6G, cc-pVDZ, cc-pVTZ, and so on. More generally, in one or more embodiments, any basis set can be suitable if like basis sets are used to represent like atoms in the molecule (e.g., representing all hydrogen atoms in a water molecule via STO-3G, representing all hydrogen atoms in a water molecule via cc-pVDZ, and so on; representing all fluorine atoms in a boron trifluoride molecule with STO-6G, representing all fluorine atoms in a boron trifluoride molecule with cc-pVTZ, and so on). Indeed, this can be the case for most symmetry operations in the basis of atomic and/or molecular orbital functions.

Now, suppose it $\pi \in S_n$ is a permutation under which the Hamiltonian is invariant. In such case, the first matrix generator 302 can, in various aspects, generate a unitary n-by-n permutation matrix R that is a second quantization representation of one or more of the point group symmetry operations 114 associated with the molecule. That is, R can be an n-by-n matrix which can operate on an n-dimensional vector of atomic/molecular orbitals of the molecule to transform the orbitals of the molecule according to one or more of the point group symmetry operations 114 (e.g., geometric rotation, reflection, inversion, and so on). In one or more embodiments, the definition of the R matrix can cause there to exist an n-qubit unitary matrix (e.g., a $2^n \times 2^n$ matrix), denoted $\hat{R}$, such that:

$$\hat{R} a_p \hat{R}^\dagger = \sum_{q=1}^{n} \langle p | R | q \rangle a_q$$

for all $1 \leq p \leq n$, where n can be a number of ferminonic modes of the molecule, and where $a_p$ and $a_q$ can be the fermionic annihilation operators associated with the molecule.

In various embodiments, since R can be a signed permutation matrix, as discussed above, it can be shown that, for all $1 \leq p \leq n$, the following holds:

$$R|p\rangle = |\pi(p)\rangle$$

By assumption, the matrix $\hat{R}$ commutes with the Hamiltonian:

$$\hat{R} H \hat{R}^\dagger = H$$

In one or more embodiments, the first matrix generator 302 can generate the matrix R and/or the matrix $\hat{R}$. However, since the matrix $\hat{R}$ can be a very large, sparse matrix (e.g., $2^n \times 2^n$), while the matrix R can be of a more manageable size (e.g., n-by-n), writing source code to perform calculations using R can, in some instances, be more computationally efficient than writing source code to perform calculations using $\hat{R}$.

Figure 4:
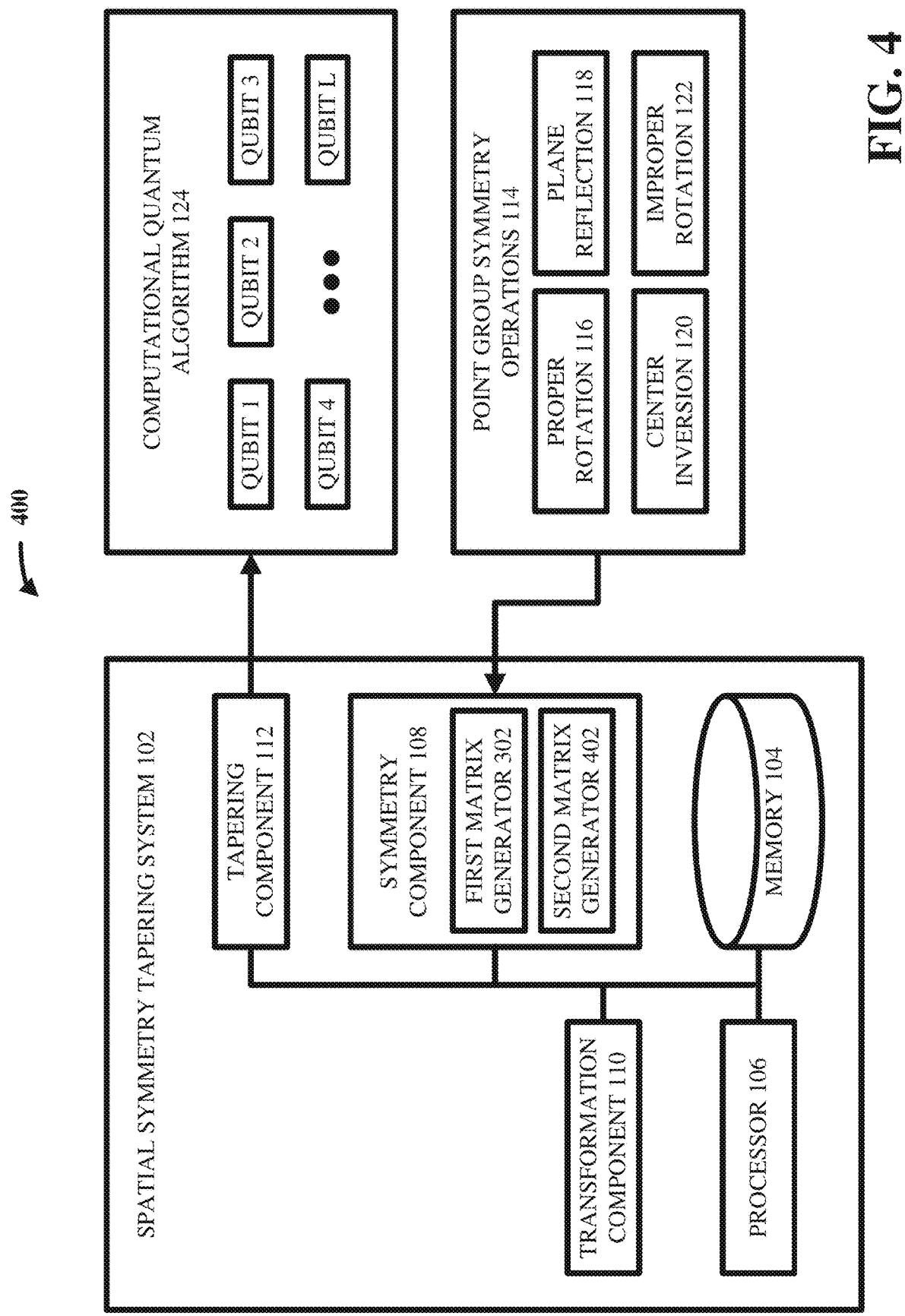
FIG. 4 illustrates a block diagram of an example, non-limiting system including a second matrix generator that facilitates precision-preserving qubit reduction based on spatial symmetries in fermionic systems in accordance with one or more embodiments described herein.

FIG. 4 illustrates a block diagram of an example, non-limiting system 400 including a second matrix generator that can facilitate precision-preserving qubit reduction based on spatial symmetries in fermionic systems in accordance with one or more embodiments described herein. As shown, the system 400 can, in various embodiments, comprise the same elements as the system 300, and can further comprise a second matrix generator 402.

Since R is a unitary matrix, it can be expressed using the matrix exponential as follows:

$$R = \exp(iG)$$

for some Hermitian matrix G of size n-by-n. It can then be shown that there exists a $2^n \times 2^n$ matrix a such that:

$$\hat{R} = \exp(i\hat{G})$$

and that:

$$\hat{G} = \sum_{p,q=1}^{n} \langle p | G | q \rangle a_p^\dagger a_q$$

In one or more embodiments, the second matrix generator 402 can generate the matrix G and/or the matrix $\hat{G}$. However, since the matrix $\hat{G}$ can be a very large, sparse matrix (e.g., $2^n \times 2^n$), while the matrix G can be of a more manageable size (e.g., n-by-n), writing source code to perform calculations using G can, in some instances, be more computationally efficient than writing source code to perform calculations using $\hat{G}$.

Figure 5:
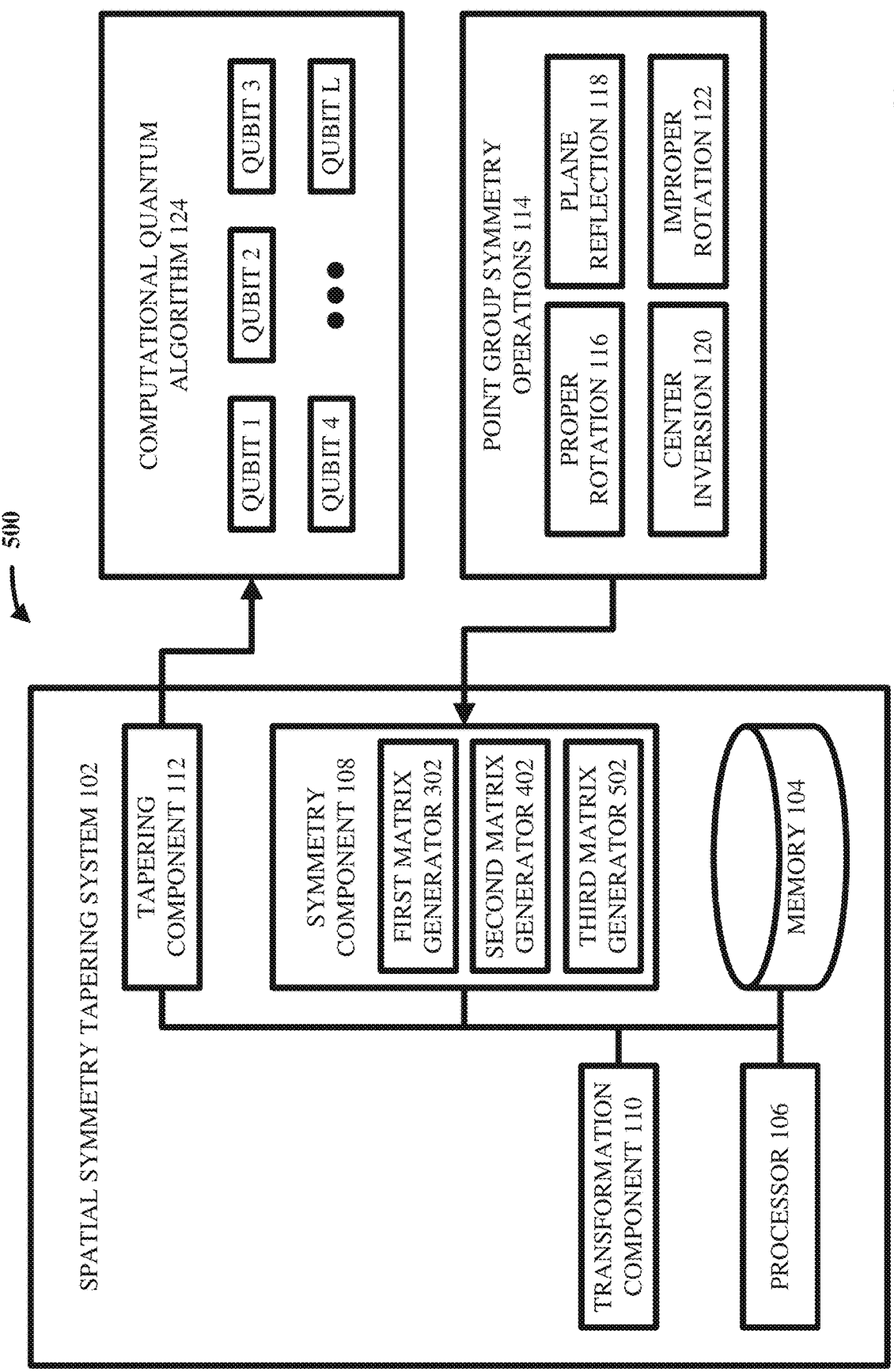
FIG. 5 illustrates a block diagram of an example, non-limiting system including a third matrix generator that facilitates precision-preserving qubit reduction based on spatial symmetries in fermionic systems in accordance with one or more embodiments described herein.

FIG. 5 illustrates a block diagram of an example, non-limiting system 500 including a third matrix generator that can facilitate precision-preserving qubit reduction based on spatial symmetries in fermionic systems in accordance with one or more embodiments described herein. As shown, the system 500 can, in various embodiments, comprise the same components as the system 400, and can further comprise a third matrix generator 502.

Given the matrix G, there exists, in various embodiments, a unitary n-by-n matrix V that diagonalizes G, such that $$V^\dagger G V = \sum_{p=1}^{n} \lambda_p |p\rangle\langle p|$$

wherein $\lambda_p$ is a real eigenvalue. Just as with the matrices R and $\hat{R}$, since V is a unitary n-by-n matrix, there exists an n-qubit (e.g., $2^n \times 2^n$) matrix $\hat{V}$, such that:

$$\hat{V} a_p \hat{V}^\dagger = \sum_{q=1}^{n} \langle p | V | q \rangle a_q$$

for all $1 \leq p \leq n$.

In one or more embodiments, the third matrix generator 502 can generate the matrix V and/or the matrix $\hat{V}$. However, since the matrix $\hat{V}$ can be a very large, sparse matrix (e.g., $2^n \times 2^n$), while the matrix V can be of a more manageable size (e.g., n-by-n), writing source code to perform calculations using V can, in some instances, be more computationally efficient than writing source code to perform calculations using $\hat{V}$.

Figure 6:
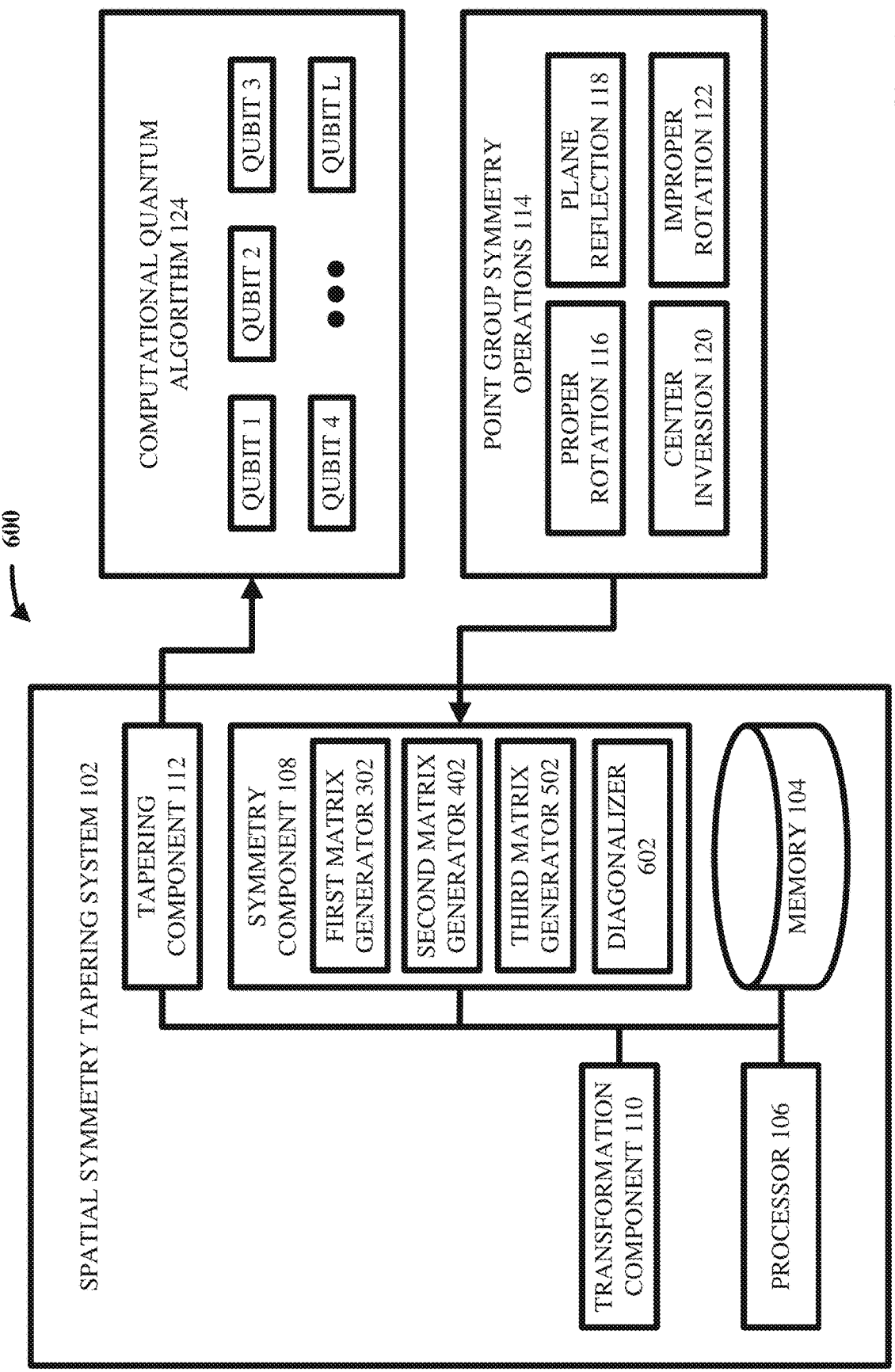
FIG. 6 illustrates a block diagram of an example, non-limiting system including a diagonalizer that facilitates precision-preserving qubit reduction based on spatial symmetries in fermionic systems in accordance with one or more embodiments described herein.

FIG. 6 illustrates a block diagram of an example, non-limiting system 600 including a diagonalizer that can facilitate precision-preserving qubit reduction based on spatial symmetries in fermionic systems in accordance with one or more embodiments described herein. As shown, the system 600 can, in various embodiments, comprise the same components as the system 500, and can further comprise a diagonalizer 602.

In various embodiments, the diagonalizer 602 can use one or more of the generated matrices (e.g., G and/or $\hat{G}$, and V and/or $\hat{V}$) to diagonalize the second quantization representation (e.g., R and/or $\hat{R}$), thereby yielding a diagonalized second quantization representation (e.g., a diagonalized matrix operator that corresponds to one or more of the point group symmetry operations 114). This new matrix operator S can be defined as follows:

$$S = \hat{V}\hat{R}\hat{V}^{\dagger} = \exp(\hat{V}\hat{G}\hat{V}^{\dagger}) = \prod_{p=1}^{n} \exp(i\lambda_p a_p^{\dagger} a_p)$$

Note that SH'=H'S, where H'=$\hat{V}$H$\hat{V}^{\dagger}$, and where H is the Hamiltonian for the given molecule. In other words, the new symmetry operator S commutes with the Hamiltonian after the Hamiltonian is transformed by the $\hat{V}$ matrix. That is, S is a symmetry of H'. Assuming that $\pi$ (e.g., an invariant permutation of the Hamiltonian) swaps some pairs of modes (e.g., swaps some atomic orbital functions in an atomic orbital vector corresponding to the molecule), then $\pi^2$ is the identity permutation. Thus, $R^2=I$, which is possible only if G has eigenvalues $\lambda_p \in \{0, \pi\}$. If M is the subset of modes p such that $\lambda_p = \pi$, it can be shown that:

$$S = \prod_{p \in M} (-1)^{a_p^{\dagger} a_p}$$

Figure 7:
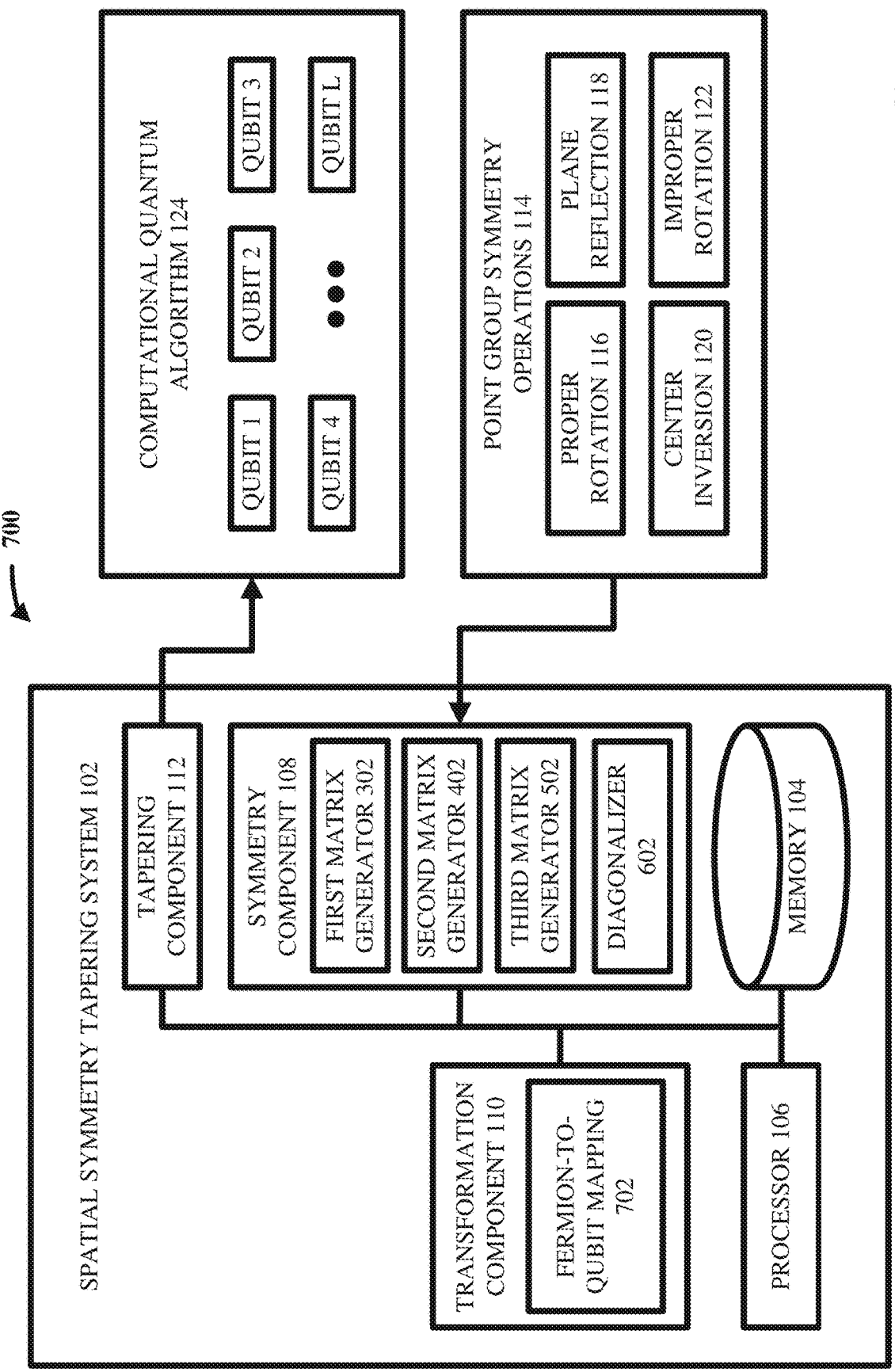
FIG. 7 illustrates a block diagram of an example, non-limiting system including a fermion-to-qubit mapping that facilitates precision-preserving qubit reduction based on spatial symmetries in fermionic systems in accordance with one or more embodiments described herein.

FIG. 7 illustrates a block diagram of an example, non-limiting system 700 including a fermion-to-qubit mapping that can facilitate precision-preserving qubit reduction based on spatial symmetries in fermionic systems in accordance with one or more embodiments described herein. As shown, the system 700 can, in one or more embodiments, comprise the same components as the system 600, and can further comprise a fermion-to-qubit mapping 702.

In various embodiments, the fermion-to-qubit mapping 702 can be any suitable mathematical transformation that converts fermionic operators (e.g., annihilation and/or creation operators) to qubit operators (e.g., Pauli gates, Hadamard gates, other quantum logic gates, and so on) that is now known or later developed (e.g., Jordan-Wigner transformation, Parity transformation, Bravyi-Kitaev transformation, Superfast Encoding transformation, Generalized Superfast Encoding transformation, Binary Tree, and so on). As mentioned above, the qubit representation of R, and thus S, in general is a summation of Pauli strings. However, the tapering-off method known in the art works only for single Pauli strings. In various aspects, the fermion-to-qubit mapping 702 can mathematically convert the diagonalized symmetry operator S from fermionic operator form to qubit operator form. In various instances, the above-described definition and generation of the matrix S can ensure that the qubit operator form of S (e.g., S after the mapping is applied) is a single Pauli string. The tapering-off procedure can then be used with the single Pauli string representing the matrix S to taper off an additional qubit (e.g., a qubit that could not have been omitted using the known tapering-off procedure alone).

In various embodiments, the Jordan-Wigner transformation can be used. If the Jordan-Wigner encoding of fermions into qubits is used, then S can become a Z-type Pauli operator, as shown:

$$S = \prod_{p \in M} (-1)^{a_p^{\dagger} a_p} \xrightarrow{\text{Jordan-Wigner}} S = \prod_{p \in M} \sigma_z^p$$

Thus, the transformed matrix S is a single Pauli string, and so the Hamiltonian H' can be simulated using a system of n-1 qubits by applying the tapering-off procedure and exploiting the Pauli symmetry S. Finally, if H includes only single-particle and two-particle operators, then so does H'.

In one or more embodiments, the G matrix need not be constructed and/or generated. Instead, the R matrix can, in some embodiments, be diagonalized directly to obtain the S matrix. The qubit operator representing S can be an operator that acts with $\sigma_z$ on qubits, j, where S(j, j)=−1. For example, if for a five dimensional S matrix the −1 eigenvalues are in position (2,2) and (4,4), then the Pauli-Z symmetry will be $Z_2 Z_4$.

It is interesting to note that various embodiments of the diagonalization procedure described herein symmetrize the orbitals in the same way as trying to put the R matrix into block diagonal irreducible representation.

Figure 8:
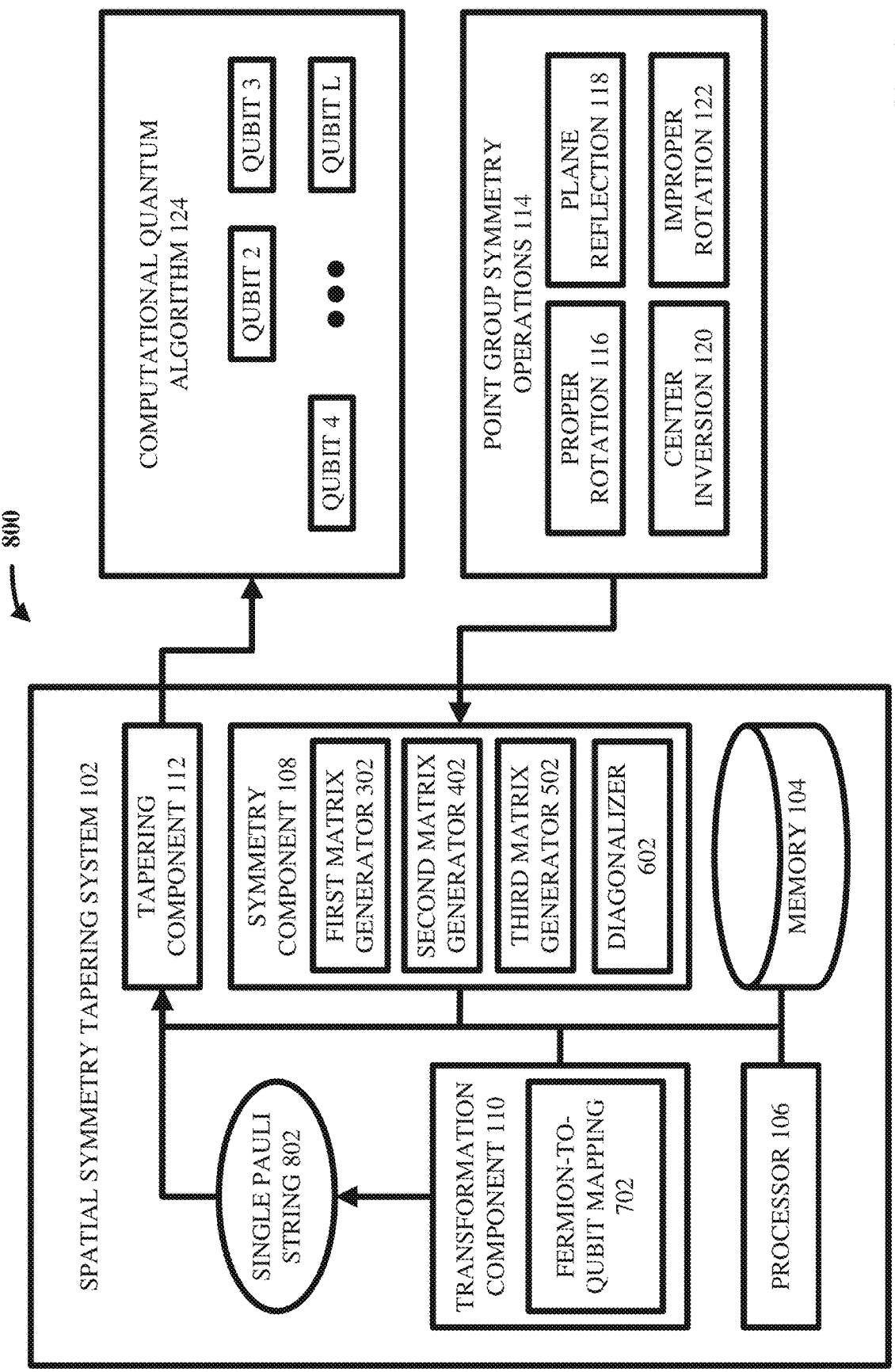
FIG. 8 illustrates a block diagram of an example, non-limiting system including a single Pauli string that facilitates precision-preserving qubit reduction based on spatial symmetries in fermionic systems in accordance with one or more embodiments described herein.

FIG. 8 illustrates a block diagram of an example, non-limiting system 800 including a single Pauli string that can facilitate precision-preserving qubit reduction based on spatial symmetries in fermionic systems in accordance with one or more embodiments described herein. As shown, the system 800 can, in various embodiments, comprise the same components as the system 700, and can further comprise a single Pauli string 802.

In various embodiments, the single Pauli string 802 can be the result of transforming the fermionic operator S, as defined and diagonalized above, into qubit operator form. The single Pauli string 802 can then be used by the tapering component 112 to taper off (e.g., eliminate) a qubit from the computational quantum algorithm 124, as explained above. For example, as shown, qubit 1 can, in various instances, be left out of the computational quantum algorithm 124 by tapering it off based on the single Pauli string 802.

In various instances, there exists a tapering-off procedure for reducing the number of qubits required to simulate the chemical properties of a given molecule. A subroutine of this procedure (e.g., finding the symmetries) can yield various symmetries of the Hamiltonian (e.g., $\tau_i \in S$). However, only those symmetries of the Hamiltonian that are single Pauli strings can be used to taper off qubits. In various instances and for various exemplary molecules, the known tapering-off procedure identifies and works with only those symmetries of the Hamiltonian that are already single Pauli strings. The inventors of the subject claimed innovation were the first to recognize that, in various instances, there can exist other symmetries of the Hamiltonian that are not initially single Pauli strings and thus cannot be identified or utilized by the known tapering-off procedure. The inventors of the subject claimed innovation discovered that, in various embodiments, those non-single Pauli strings can correspond to the geometric symmetries (e.g., rotations, reflections, inversions) of the molecule. Various embodiments of the subject claimed innovation provide a novel, step-by-step procedure for using such geometric symmetries to generate additional single Pauli strings that can be used to taper off additional qubits, thereby eliminating more qubits from the computational quantum algorithm than can the known tapering-off procedure alone.

FIG. 9 illustrates a diagram 900 of example, non-limiting matrices representing spatial point group symmetry operations of a water molecule that can be used to facilitate precision-preserving qubit reduction based on spatial symmetries in fermionic systems in accordance with one or more embodiments described herein.

As shown, the diagram 900 depicts a water molecule 902 positioned on Cartesian axes and two exemplary matrices 904 and 906 that can represent point group symmetry operations associated with the water molecule in the second quantized formalism (e.g., in the basis of atomic orbitals).

For instance, the matrix 904 can represent a matrix operator that corresponds to a reflection through the x-z plane of the depicted water molecule 902. Since the oxygen atom and both hydrogen atoms are in the x-z plane, all the atoms stay where they are after the reflection, with the only difference being that the $2p_y$ orbitals of the oxygen atom pick up a phase (e.g., the $2p_y$ orbitals switch places). This swap can be accomplished by the elements 908 in the matrix 904. In various aspects, since the matrix 904 is diagonal, it can be shown that the qubit operator representation of the matrix 904 is a single Pauli string. This is why the known tapering-off procedure was able to generate and utilize this particular symmetry (e.g., this y-z reflection can correspond to the $\sigma_4^z \sigma_{11}^z$ symmetry obtained for a water molecule using the Jordan-Wigner transformation, as shown in FIG. 2, since the elements 908 can correspond to the fourth and eleventh elements along the diagonal of the matrix 904).

In various instances, the matrix 906 can represent a matrix operator that corresponds to a reflection through the y-z plane of the depicted water molecule 902. Since the oxygen atom is in the y-z plane but the hydrogen atoms are not, the two hydrogen atoms switch places and the oxygen atom stays where it is after the reflection, with the $2p_x$ orbitals of the oxygen atom picking up a phase. The swapping of the $2p_x$ orbitals can be accomplished by the elements 910 in the matrix 906. In various cases, the swapping of the hydrogen atoms can be accomplished by the elements 912 in the matrix 906. Since this matrix 906 is not diagonal, it can be shown that the qubit operator representation of this y-z reflection (e.g., of this matrix 906) is not a single Pauli string. This is the reason that it did not show up at all in the known tapering-off procedure. In various instances, the matrix 906 can correspond to the above-described R matrix and can be diagonalized into the new symmetry operator S, as described above. Once diagonalized as taught herein, the qubit operator representation of the diagonal matrix corresponding to the matrix 906 can be a single Pauli string. The single Pauli string can then be used to taper off qubits, thus resulting in elimination of at least one more qubit than the known tapering-off procedure alone.

Figure 10:
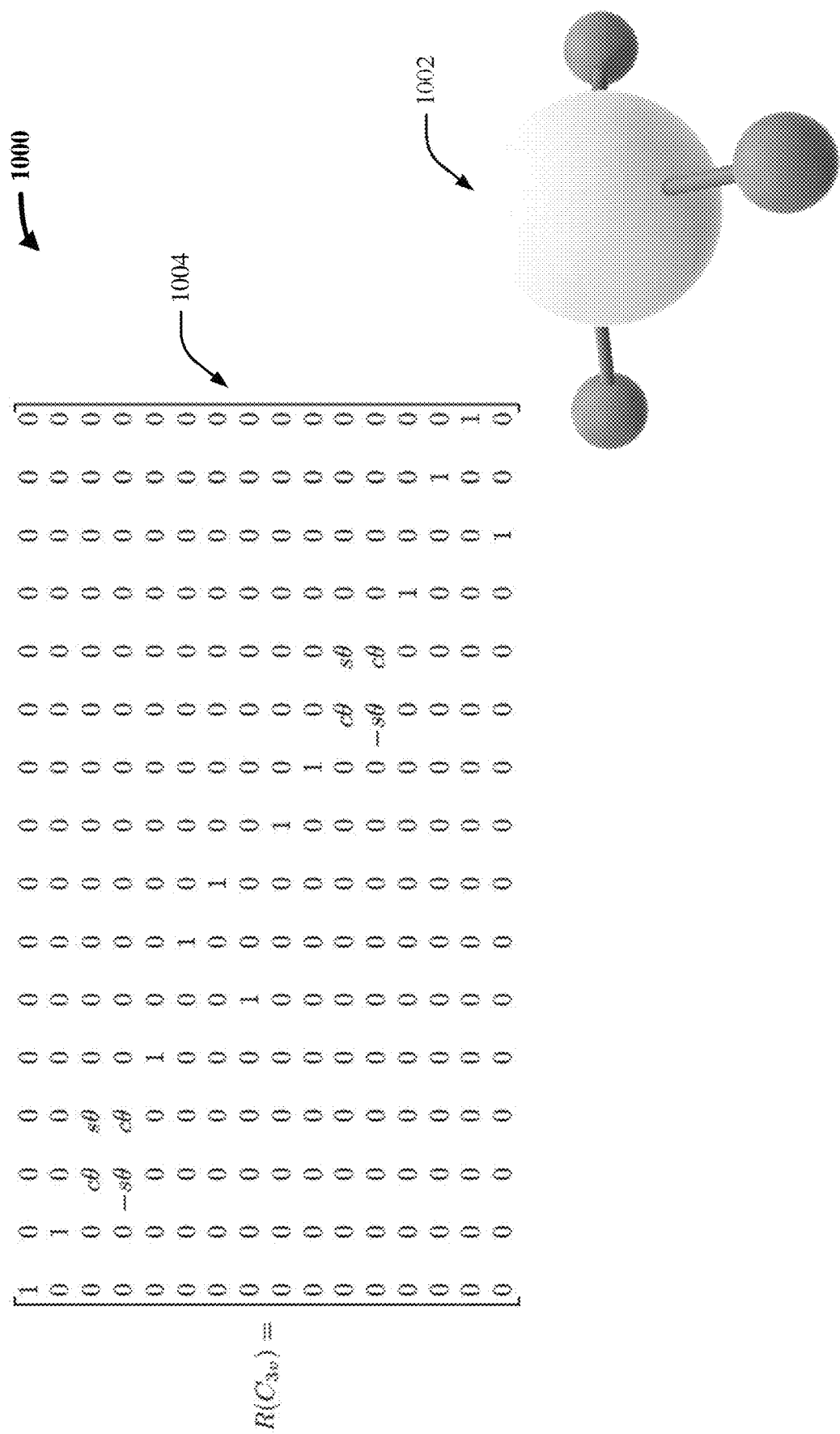
FIG. 10 illustrates a diagram of an example, non-limiting matrix representing a spatial point group symmetry operation of an ammonia molecule that can be used to facilitate precision-preserving qubit reduction based on spatial symmetries in fermionic systems in accordance with one or more embodiments described herein.

FIG. 10 illustrates a diagram 1000 of an example, non-limiting matrix representing a spatial point group symmetry operation of an ammonia molecule that can be used to facilitate precision-preserving qubit reduction based on spatial symmetries in fermionic systems in accordance with one or more embodiments described herein.

As shown, FIG. 10 depicts an ammonia molecule 1002 and an exemplary matrix 1004 that can represent point group symmetry operations associated with the ammonia molecule in the second quantized formalism (e.g., in the basis of atomic orbitals). For instance, the matrix 1004 can represent a matrix operator that corresponds to a $C_3$ rotation (e.g., a 120° rotation) of the ammonia molecule about its principal axis. As shown, the matrix 1004 is not diagonal, and so it can be shown that the qubit operator representation of the matrix 1004 is not a single Pauli string. Thus, this symmetry cannot be found using the known tapering-off procedure alone. In various instances, the matrix 1004 can correspond to the above-described R matrix and can thus be diagonalized as taught herein to form the S operator. After this diagonalization, it can be shown that the qubit operator representation of the diagonal matrix corresponding to the matrix 1004 is a single Pauli string that can be used to taper off additional qubits.

FIG. 11 illustrates a table 1100 of example, non-limiting results from precision-preserving qubit reduction based on spatial symmetries in fermionic systems in accordance with one or more embodiments described herein.

Table 1100 presents exemplary results for various molecules that were studied along with the number of qubits that were able to be tapered off based on spatial point group symmetries. As shown, experiments were run for molecules such as hydrogen ($H_2$), hydrogen chloride (HCl), beryllium hydride ($BeH_2$), ammonia ($NH_3$), water ($H_2O$), ethylene ($C_2H_4$), boron trifluoride ($BF_3$), lithium hydride (LiH), carbon dioxide ($CO_2$), and acetylene ($C_2H_2$). In various embodiments, the subject claimed innovation can be used with any molecule having an associated spatial point group symmetry.

The "qubits tapered" in table 1100 demonstrates the total number of qubits tapered for each molecule using embodiments of the subject claimed innovation. It can be shown that, for each molecule, one additional qubit can be tapered off by leveraging point group symmetries than can be tapered by the known tapering-off procedure alone. For instance, for a water molecule, four qubits can be tapered off using the subject claimed innovation (as shown in table 1100), while only three can be tapered off using the known procedure. Similarly, for an ammonia molecule, three qubits can be tapered off using the subject claimed innovation (as shown in table 1100), while only two can be tapered off using the known procedure.

What follows is an exemplary discussion of three molecules from the table 1100 to illustrate three points. First, the hydrogen molecule is discussed to demonstrate the procedure of tapering off qubits using spatial symmetries. Second, the beryllium hydride molecule is discussed to demonstrate that spatial symmetries can, in various embodiments, be used to reduce more qubits than the tapering-off qubits procedure. Third, the ammonia molecule is discussed to show that only an abelian subgroup of the symmetry point group can be used to taper off qubits.

First, consider the hydrogen molecule. As explained above, a basis set is picked such that the operation corresponding to the spatial symmetries ends up being a permutation matrix. In various cases, the bond length of the hydrogen molecule can be 0.7414 Å, and the basis set can be STO-3G, where a single 1s orbital is placed on each of the hydrogen atoms. So, both $C_2$ (rotation about z-axis by 180°) and $\sigma_{yz}$ (reflection through y-z plane) will have the net effect of swapping the two hydrogen atoms. This corresponds to swapping the 1s orbitals and hence the rotation matrix, R can be a permutation matrix:

$$\begin{bmatrix} 0 & 1 & 0 & 0 \\ 1 & 0 & 0 & 0 \\ 0 & 0 & 0 & 1 \\ 0 & 0 & 1 & 0 \end{bmatrix}$$

It can be checked that the Hamiltonian does remain the same under this permutation of the fermionic modes. The G matrix corresponding to the R matrix can then be diagonalized as taught herein, and a qubit can be tapered off.

Second, consider the beryllium hydride molecule. For beryllium hydride, the total number of qubits that can be tapered off using point group symmetries are five, as shown in table 1100. In contrast, with the known tapering-off qubit procedure, only four qubits can be eliminated. The geometry used is linear where the bond length between beryllium and hydrogen is 1.291 Å for both bonds.

Given this geometry, the symmetries that could be represented using a generalized permutation matrix are, $\sigma_{xy}$ (reflection in x-y plane), $\sigma_{yz}$ (reflection in y-z plane), and $\sigma_{xz}$ (reflection in x-z plane). The qubit operators for the R operator corresponding to $\sigma_{xy}$ and $\sigma_{xz}$ turn out to be single qubit operators (e.g., single Pauli strings), and the final qubit operators for these symmetries match the symmetries found using the tapering off qubit procedure. The unitary, R, for the symmetry, $\sigma_{yz}$, on the other hand, is not diagonal and the qubit operator representation is a non-single sum of Pauli strings. For this reason, the symmetry $\sigma_{yz}$ is not observed using the known tapering-off qubit procedure. But, the spatial symmetry can be used to taper off a qubit using various embodiments of the subject claimed innovation (e.g., the particular diagonalization procedure explained above).

Third, consider the ammonia molecule. Ammonia belongs to the symmetry group, $C_{3v}$. In the symmetry group, there are two rotation operators and three reflection operators. The two rotation operators form a class and so do the three reflection operators. If the symmetry group were abelian, the qubit count could be reduced by one for each class. However, since the symmetry operators in two classes do not commute (e.g., not abelian), we can reduce the qubit count by just one corresponding to one of the symmetries. Further, as per the formalism developed above, the unitary operator R should square to identity. This implies the only choice available for the ammonia molecule is the reflection operator. It should be noted that this symmetry did not appear using the known tapering-off qubit procedure.

The following discussion explains how to pick the correct eigenvalues when tapering off qubits based on spatial point group symmetries. As mentioned above, R should square to identity. This implies that the eigenvalues of the R operator must be ±1. Let V be the matrix that puts the R operator in diagonal form and S be the n-by-n diagonal matrix corresponding to R, as described above. Assume the Jordan-Wigner mapping is used, and let T={x|S(x, x)=−1}. Then, the qubit operator representation of S is an operator with $\sigma_z$ on a set of qubits T (e.g., if for a 5×5 S matrix the −1 eigenvalues are in position (2,2) and (4,4), then the Pauli-Z symmetry will be $Z_2Z_4$).

Once all the symmetries, S, of the Hamiltonian are constructed, the correct eigensector of the symmetry should be picked. This can be done using the relation between the $\sigma_z$ qubit operator and the occupation number in the Jordan-Wigner transform:

$$\sigma_z^i = a_i^\dagger a_i - 1$$

So, an occupied fermionic mode corresponds to the eigenvalue −1, and an unoccupied fermionic mode corresponds to the eigenvalue +1, of the $\sigma_z$ operator. This implies that a symmetry operator, S, which is a Pauli-Z string on, for instance, a set Q of qubits, is related to the parity operator of fermionic modes stored in those Q qubits. In various cases, as explained above, one can start with atomic orbitals and then transform them with a V matrix so as to get R into a diagonal form (e.g., S). Consequently, the occupation numbers of these transformed orbitals are stored in the qubits. Based on whether the orbital is occupied or unoccupied in a given symmetry sector, it is possible to figure out the correct eigensector corresponding to the symmetry.

For example, in case of $BeH_2$ molecule, there are 14 orbitals in total with six electrons. The symmetries corresponding to conservation of spin up electrons and spin down electrons are $S_1 = \sigma_z^1 \sigma_z^2 \sigma_z^3 \sigma_z^4 \sigma_z^5 \sigma_z^6 \sigma_z^7$ and $S_2 = \sigma_z^8 \sigma_z^9 \sigma_z^{10} \sigma_z^{11} \sigma_z^{12} \sigma_z^{13} \sigma_z^{14}$, respectively. Since, there are six electrons in total, each spin sector will have three electrons. Thus, the correct sector for each of the symmetries, $S_1$ and $S_2$ is the one with −1 eigenvalue.

With respect to molecular orbitals, most of the quantum chemistry software can recognize the symmetry from geometry and can construct the molecular orbitals for the Hartree-Fock procedure accordingly. This means that molecular orbitals can be already symmetrized corresponding to different irreps and that the symmetry operators can be $Z_2$ symmetries. One way to construct $Z_2$ symmetries can be to start from R operators, as discussed above, and then to get the Pauli-Z string corresponding to the symmetry operator. The R operator can require the knowledge of the molecular orbitals in terms of atomic orbitals, and can be obtained from the quantum chemistry software.

Another method to obtain the symmetries can be to just run the subroutine, in tapering off qubits, to find the $Z_2$ symmetries. This process can be a little bit more efficient as it is automated. However, the benefit of starting from R matrices is that one gets an intuitive understanding of the symmetries.

It was verified that, for multiple Hamiltonians, the tapered off qubit Hamiltonian does, in fact, have the same eigenspectrum.

Figure 12:
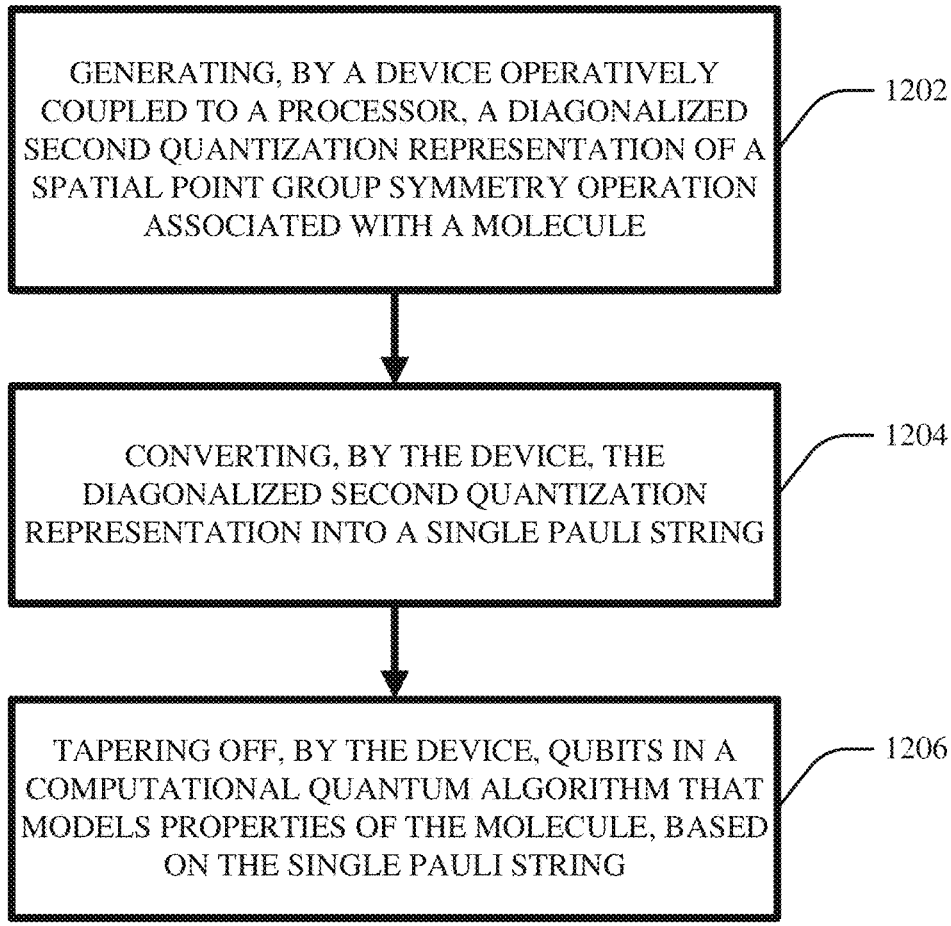
FIG. 12 illustrates a flow diagram of an example, non-limiting computer-implemented method that facilitates precision-preserving qubit reduction based on spatial symmetries in fermionic systems in accordance with one or more embodiments described herein.

FIG. 12 illustrates a flow diagram of an example, non-limiting computer-implemented method 1200 that can facilitate precision-preserving qubit reduction based on spatial symmetries in fermionic systems in accordance with one or more embodiments described herein.

Act 1202 can comprise generating, by a device operatively coupled to a processor, a diagonalized second quantization representation (e.g., the S matrix, as defined above with respect to FIG. 6) of a spatial point group symmetry operation (e.g., one or more of the point group symmetry operations 114) that is associated with a molecule.

Act 1204 can comprise converting, by the device, the diagonalized second quantization representation into a single Pauli string, as in one or more embodiments taught above.

Act 1206 can comprise tapering off (e.g., via the known tapering-off technique), by the device, one or more qubits in a computational quantum algorithm (e.g., computational quantum algorithm 124) that models properties of the molecule, based on the single Pauli string, as taught in one or more embodiments above.

Figure 13:
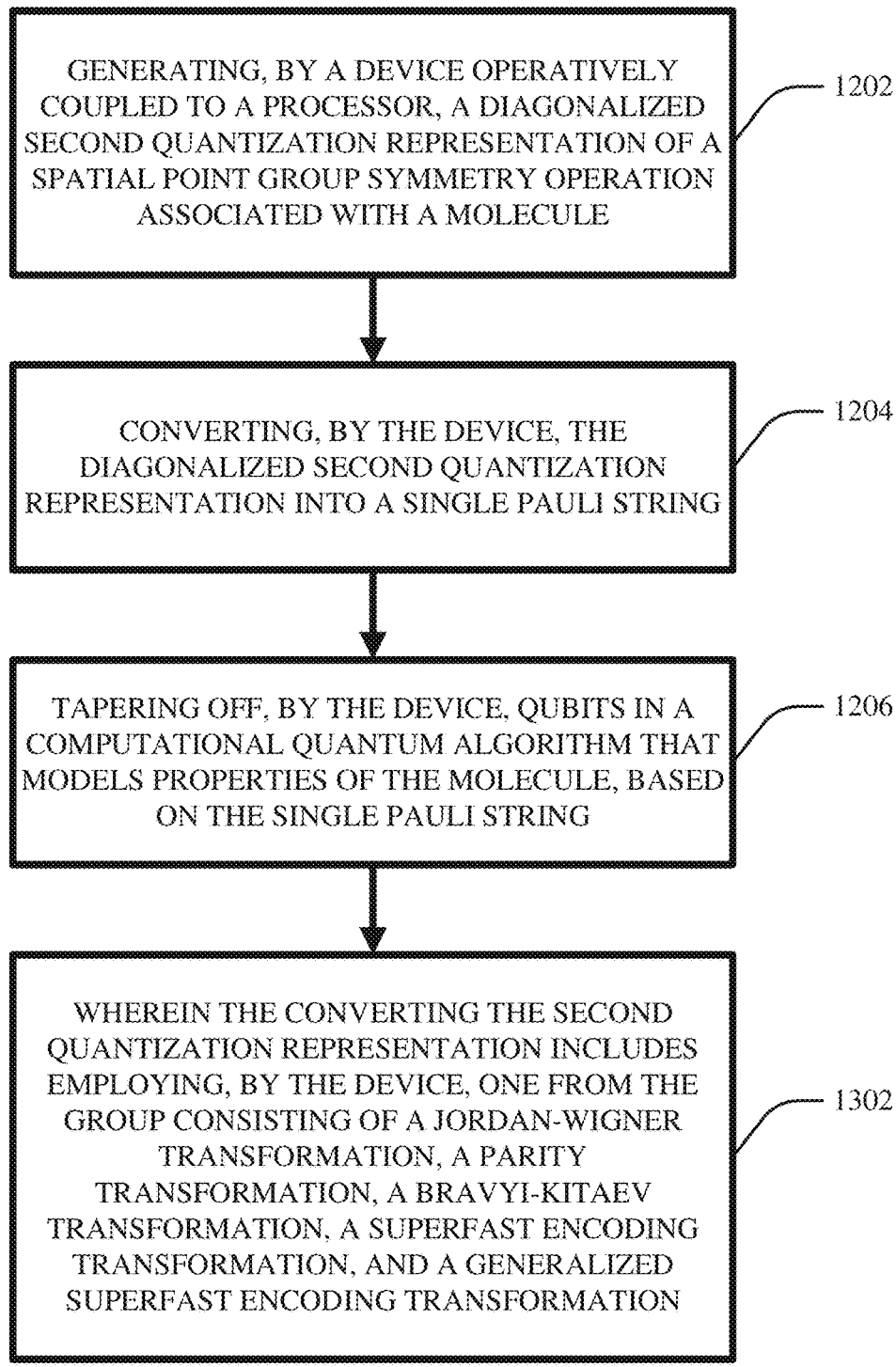
FIG. 13 illustrates a flow diagram of an example, non-limiting computer-implemented method that facilitates precision-preserving qubit reduction based on spatial symmetries in fermionic systems in accordance with one or more embodiments described herein.

FIG. 13 illustrates a flow diagram of an example, non-limiting computer-implemented method 1300 that can facilitate precision-preserving qubit reduction based on spatial symmetries in fermionic systems in accordance with one or more embodiments described herein. As shown, the computer-implemented method 1300 can, in various embodiments, comprise the same acts as the computer-implemented method 1200, and can further comprise act 1302.

Act 1302 can comprise wherein the converting the second quantization representation includes employing, by the device, one from the group consisting of a Jordan-Wigner transformation, a Parity transformation, a Bravyi-Kitaev transformation, a Superfast Encoding transformation, and/or a Generalized Superfast Encoding transformation.

Figure 14:
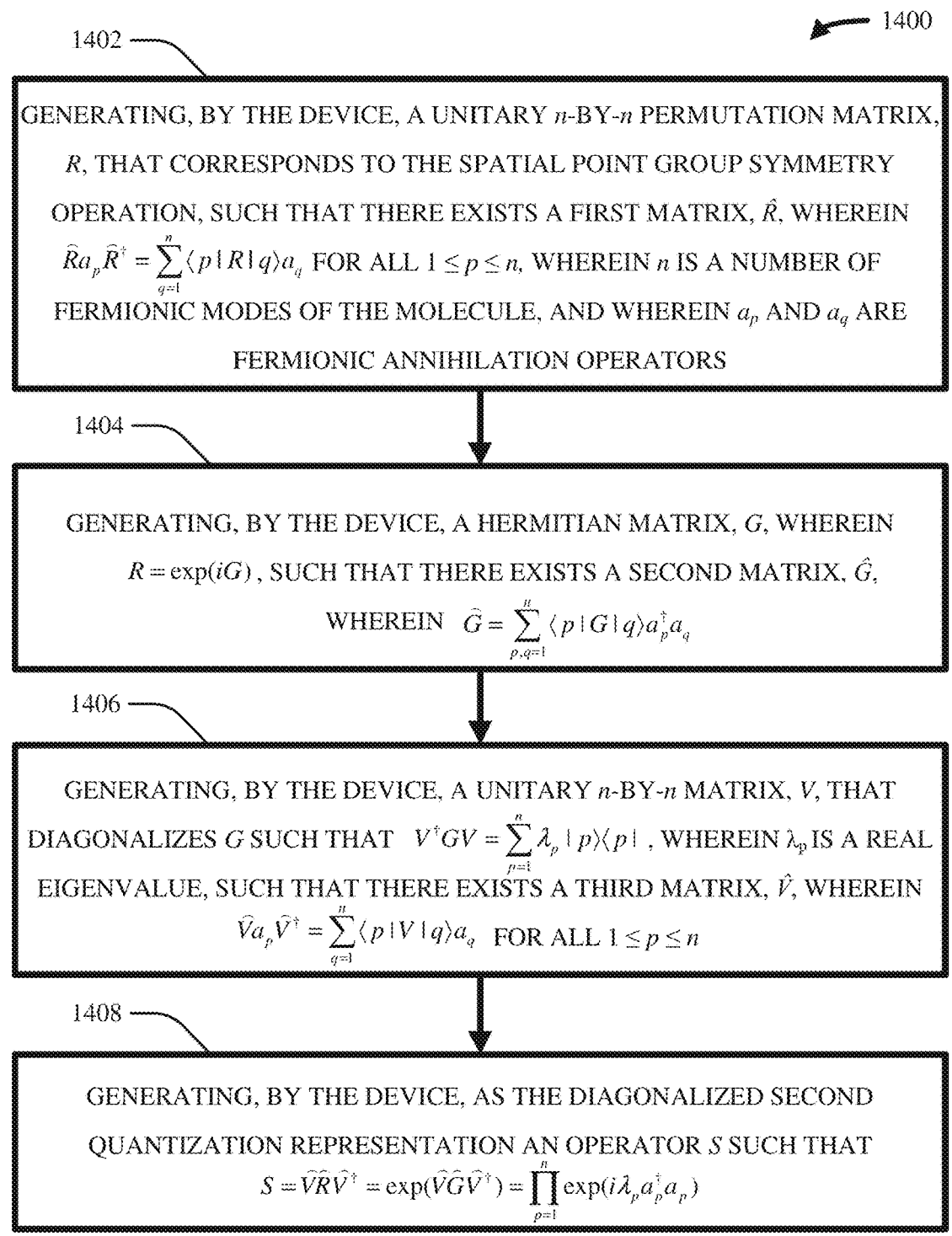
FIG. 14 illustrates a flow diagram of an example, non-limiting computer-implemented method that facilitates generation of a diagonalized second quantization representation of a spatial point group symmetry operation in accordance with one or more embodiments described herein.

FIG. 14 illustrates a flow diagram of an example, non-limiting computer-implemented method 1400 that can facilitate generation of a diagonalized second quantization representation of a spatial point group symmetry operation in accordance with one or more embodiments described herein. That is, the computer-implemented method 1400 can represent a subroutine to perform act 1202 in computer-implemented method 1200.

Act 1402 can include generating, by the device, a unitary n-by-n permutation matrix, R, that corresponds to the spatial point group symmetry operation, such that there exists a first matrix, $\hat{R}$, wherein $\hat{R}a_p \hat{R}^\dagger = \Sigma_{q=1}^n \langle p|R|q \rangle a_q$ for all $1 \leq p \leq n$, wherein n is a number of fermionic modes of the molecule, and wherein $a_p$ and $a_q$ are fermionic annihilation operators.

Act 1404 can include generating, by the device, a Hermitian matrix, G, wherein R=exp(iG), such that there exists a second matrix, $\hat{G}$, wherein $\hat{G} = \Sigma_{p,q=1}^n \langle p|G|q \rangle \mathcal{P} a_p^\dagger a_q$.

Act 1404 can include generating, by the device, a unitary n-by-n matrix, V, that diagonalizes G such that $V^\dagger GV = \Sigma_{p=1}^n \lambda_p |p\rangle \langle p|$, wherein $\lambda_p$ is a real eigenvalue, such that there exists a third matrix, $\hat{V}$, wherein $\hat{V} a_p \hat{V}^\dagger = \Sigma_{q=1}^n \mathcal{P} p|V|q \mathcal{P} a_q$ for all $1 \leq p \leq n$.

Act 1406 can include generating, by the device, as the diagonalized second quantization representation an operator S such that $S = \hat{V}\hat{R}\hat{V}^\dagger = \exp(\hat{V}\hat{G}\hat{V}^\dagger) = \Pi_{p=1}^n \exp(i\lambda_p a_p^\dagger a_p)$.

Figure 15:
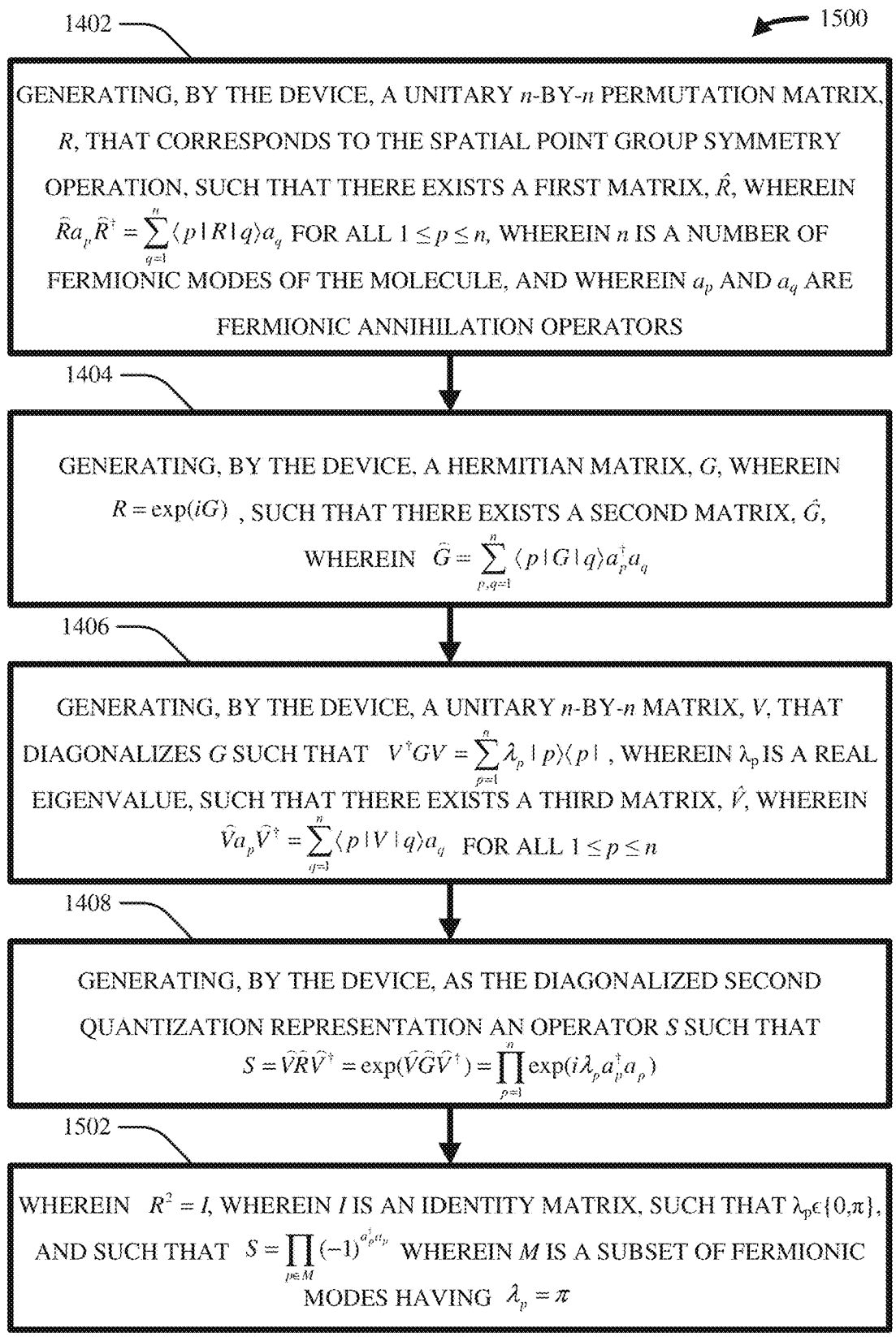
FIG. 15 illustrates a flow diagram of an example, non-limiting computer-implemented method that facilitates generation of a diagonalized second quantization representation of a spatial point group symmetry operation in accordance with one or more embodiments described herein.

FIG. 15 illustrates a flow diagram of an example, non-limiting computer-implemented method 1500 that can facilitate generation of a diagonalized second quantization representation of a spatial point group symmetry operation in accordance with one or more embodiments described herein. As shown, the computer-implemented method 1500 can, in various embodiments, comprise the same acts as the computer-implemented method 1400, and can further comprise act 1502.

Act 1502 can include wherein $R^2=I$, wherein I is an identity matrix, such that $\lambda_p \in \{0, \pi\}$, and such that $S = \Pi_{p \in M} (-1)^{a_p^\dagger a_p}$ wherein M is a subset of fermionic modes having $\lambda_p = \pi$.

Figure 16:
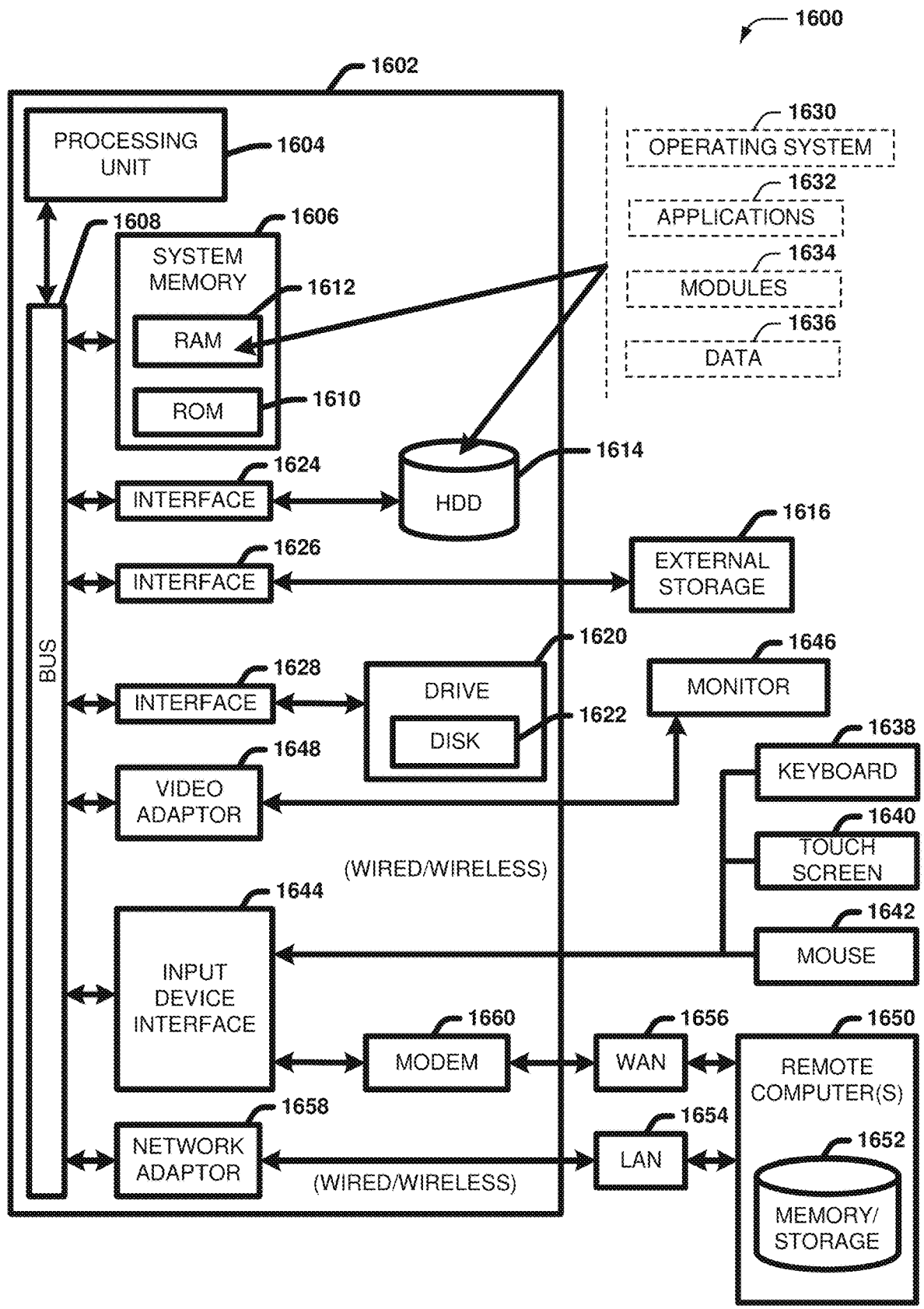
FIG. 16 illustrates a block diagram of an example, non-limiting operating environment in which one or more embodiments described herein can be facilitated.

In order to provide additional context for various embodiments described herein, FIG. 16 and the following discussion are intended to provide a general description of a suitable computing environment 1600 in which the various embodiments of the embodiment described herein can be implemented. While the embodiments have been described above in the general context of computer-executable instructions that can run on one or more computers, those skilled in the art will recognize that the embodiments can be also implemented in combination with other program modules and/or as a combination of hardware and software.

Generally, program modules include routines, programs, components, data structures, etc., that perform particular tasks or implement particular abstract data types. Moreover, those skilled in the art will appreciate that the inventive methods can be practiced with other computer system configurations, including single-processor or multiprocessor computer systems, minicomputers, mainframe computers, Internet of Things (IoT) devices, distributed computing systems, as well as personal computers, hand-held computing devices, microprocessor-based or programmable consumer electronics, and the like, each of which can be operatively coupled to one or more associated devices.

The illustrated embodiments of the embodiments herein can be also practiced in distributed computing environments where certain tasks are performed by remote processing devices that are linked through a communications network. In a distributed computing environment, program modules can be located in both local and remote memory storage devices.

Computing devices typically include a variety of media, which can include computer-readable storage media, machine-readable storage media, and/or communications media, which two terms are used herein differently from one another as follows. Computer-readable storage media or machine-readable storage media can be any available storage media that can be accessed by the computer and includes both volatile and nonvolatile media, removable and non-removable media. By way of example, and not limitation, computer-readable storage media or machine-readable storage media can be implemented in connection with any method or technology for storage of information such as computer-readable or machine-readable instructions, program modules, structured data or unstructured data.

Computer-readable storage media can include, but are not limited to, random access memory (RAM), read only memory (ROM), electrically erasable programmable read only memory (EEPROM), flash memory or other memory technology, compact disk read only memory (CD-ROM), digital versatile disk (DVD), Blu-ray disc (BD) or other optical disk storage, magnetic cassettes, magnetic tape, magnetic disk storage or other magnetic storage devices, solid state drives or other solid state storage devices, or other tangible and/or non-transitory media which can be used to store desired information. In this regard, the terms "tangible" or "non-transitory" herein as applied to storage, memory or computer-readable media, are to be understood to exclude only propagating transitory signals per se as modifiers and do not relinquish rights to all standard storage, memory or computer-readable media that are not only propagating transitory signals per se.

Computer-readable storage media can be accessed by one or more local or remote computing devices, e.g., via access requests, queries or other data retrieval protocols, for a variety of operations with respect to the information stored by the medium.

Communications media typically embody computer-readable instructions, data structures, program modules or other structured or unstructured data in a data signal such as a modulated data signal, e.g., a carrier wave or other transport mechanism, and includes any information delivery or transport media. The term "modulated data signal" or signals refers to a signal that has one or more of its characteristics set or changed in such a manner as to encode information in one or more signals. By way of example, and not limitation, communication media include wired media, such as a wired network or direct-wired connection, and wireless media such as acoustic, RF, infrared and other wireless media.

With reference again to FIG. 16, the example environment 1600 for implementing various embodiments of the aspects described herein includes a computer 1602, the computer 1602 including a processing unit 1604, a system memory 1606 and a system bus 1608. The system bus 1608 couples system components including, but not limited to, the system memory 1606 to the processing unit 1604. The processing unit 1604 can be any of various commercially available processors. Dual microprocessors and other multi-processor architectures can also be employed as the processing unit 1604.

The system bus 1608 can be any of several types of bus structure that can further interconnect to a memory bus (with or without a memory controller), a peripheral bus, and a local bus using any of a variety of commercially available bus architectures. The system memory 1606 includes ROM 1610 and RAM 1612. A basic input/output system (BIOS) can be stored in a non-volatile memory such as ROM, erasable programmable read only memory (EPROM), EEPROM, which BIOS contains the basic routines that help to transfer information between elements within the computer 1602, such as during startup. The RAM 1612 can also include a high-speed RAM such as static RAM for caching data.

The computer 1602 further includes an internal hard disk drive (HDD) 1614 (e.g., EIDE, SATA), one or more external storage devices 1616 (e.g., a magnetic floppy disk drive (FDD) 1616, a memory stick or flash drive reader, a memory card reader, etc.) and a drive 1620, e.g., such as a solid state drive, an optical disk drive, which can read or write from a disk 1622, such as a CD-ROM disc, a DVD, a BD, etc. Alternatively, where a solid state drive is involved, disk 1622 would not be included, unless separate. While the internal HDD 1614 is illustrated as located within the computer 1602, the internal HDD 1614 can also be configured for external use in a suitable chassis (not shown). Additionally, while not shown in environment 1600, a solid state drive (SSD) could be used in addition to, or in place of, an HDD 1614. The HDD 1614, external storage device(s) 1616 and drive 1620 can be connected to the system bus 1608 by an HDD interface 1624, an external storage interface 1626 and a drive interface 1628, respectively. The interface 1624 for external drive implementations can include at least one or both of Universal Serial Bus (USB) and Institute of Electrical and Electronics Engineers (IEEE) 1394 interface technologies. Other external drive connection technologies are within contemplation of the embodiments described herein.

The drives and their associated computer-readable storage media provide nonvolatile storage of data, data structures, computer-executable instructions, and so forth. For the computer 1602, the drives and storage media accommodate the storage of any data in a suitable digital format. Although the description of computer-readable storage media above refers to respective types of storage devices, it should be appreciated by those skilled in the art that other types of storage media which are readable by a computer, whether presently existing or developed in the future, could also be used in the example operating environment, and further, that any such storage media can contain computer-executable instructions for performing the methods described herein.

A number of program modules can be stored in the drives and RAM 1612, including an operating system 1630, one or more application programs 1632, other program modules 1634 and program data 1636. All or portions of the operating system, applications, modules, and/or data can also be cached in the RAM 1612. The systems and methods described herein can be implemented utilizing various commercially available operating systems or combinations of operating systems.

Computer 1602 can optionally comprise emulation technologies. For example, a hypervisor (not shown) or other intermediary can emulate a hardware environment for operating system 1630, and the emulated hardware can optionally be different from the hardware illustrated in FIG. 16. In such an embodiment, operating system 1630 can comprise one virtual machine (VM) of multiple VMs hosted at computer 1602. Furthermore, operating system 1630 can provide runtime environments, such as the Java runtime environment or the .NET framework, for applications 1632. Runtime environments are consistent execution environments that allow applications 1632 to run on any operating system that includes the runtime environment. Similarly, operating system 1630 can support containers, and applications 1632 can be in the form of containers, which are lightweight, standalone, executable packages of software that include, e.g., code, runtime, system tools, system libraries and settings for an application.

Further, computer 1602 can be enabled with a security module, such as a trusted processing module (TPM). For instance with a TPM, boot components hash next in time boot components, and wait for a match of results to secured values, before loading a next boot component. This process can take place at any layer in the code execution stack of computer 1602, e.g., applied at the application execution level or at the operating system (OS) kernel level, thereby enabling security at any level of code execution.

A user can enter commands and information into the computer 1602 through one or more wired/wireless input devices, e.g., a keyboard 1638, a touch screen 1640, and a pointing device, such as a mouse 1642. Other input devices (not shown) can include a microphone, an infrared (IR) remote control, a radio frequency (RF) remote control, or other remote control, a joystick, a virtual reality controller and/or virtual reality headset, a game pad, a stylus pen, an image input device, e.g., camera(s), a gesture sensor input device, a vision movement sensor input device, an emotion or facial detection device, a biometric input device, e.g., fingerprint or iris scanner, or the like. These and other input devices are often connected to the processing unit 1604 through an input device interface 1644 that can be coupled to the system bus 1608, but can be connected by other interfaces, such as a parallel port, an IEEE 1394 serial port, a game port, a USB port, an IR interface, a BLUETOOTH® interface, etc.

A monitor 1646 or other type of display device can be also connected to the system bus 1608 via an interface, such as a video adapter 1648. In addition to the monitor 1646, a computer typically includes other peripheral output devices (not shown), such as speakers, printers, etc.

The computer 1602 can operate in a networked environment using logical connections via wired and/or wireless communications to one or more remote computers, such as a remote computer(s) 1650. The remote computer(s) 1650 can be a workstation, a server computer, a router, a personal computer, portable computer, microprocessor-based entertainment appliance, a peer device or other common network node, and typically includes many or all of the elements described relative to the computer 1602, although, for purposes of brevity, only a memory/storage device 1652 is illustrated. The logical connections depicted include wired/wireless connectivity to a local area network (LAN) 1654 and/or larger networks, e.g., a wide area network (WAN) 1656. Such LAN and WAN networking environments are commonplace in offices and companies, and facilitate enterprise-wide computer networks, such as intranets, all of which can connect to a global communications network, e.g., the Internet.

When used in a LAN networking environment, the computer 1602 can be connected to the local network 1654 through a wired and/or wireless communication network interface or adapter 1658. The adapter 1658 can facilitate wired or wireless communication to the LAN 1654, which can also include a wireless access point (AP) disposed thereon for communicating with the adapter 1658 in a wireless mode.

When used in a WAN networking environment, the computer 1602 can include a modem 1660 or can be connected to a communications server on the WAN 1656 via other means for establishing communications over the WAN 1656, such as by way of the Internet. The modem 1660, which can be internal or external and a wired or wireless device, can be connected to the system bus 1608 via the input device interface 1644. In a networked environment, program modules depicted relative to the computer 1602 or portions thereof, can be stored in the remote memory/storage device 1652. It will be appreciated that the network connections shown are example and other means of establishing a communications link between the computers can be used.

When used in either a LAN or WAN networking environment, the computer 1602 can access cloud storage systems or other network-based storage systems in addition to, or in place of, external storage devices 1616 as described above, such as but not limited to a network virtual machine providing one or more aspects of storage or processing of information. Generally, a connection between the computer 1602 and a cloud storage system can be established over a LAN 1654 or WAN 1656 e.g., by the adapter 1658 or modem 1660, respectively. Upon connecting the computer 1602 to an associated cloud storage system, the external storage interface 1626 can, with the aid of the adapter 1658 and/or modem 1660, manage storage provided by the cloud storage system as it would other types of external storage. For instance, the external storage interface 1626 can be configured to provide access to cloud storage sources as if those sources were physically connected to the computer 1602.

The computer 1602 can be operable to communicate with any wireless devices or entities operatively disposed in wireless communication, e.g., a printer, scanner, desktop and/or portable computer, portable data assistant, communications satellite, any piece of equipment or location associated with a wirelessly detectable tag (e.g., a kiosk, news stand, store shelf, etc.), and telephone. This can include Wireless Fidelity (Wi-Fi) and BLUETOOTH® wireless technologies. Thus, the communication can be a predefined structure as with a conventional network or simply an ad hoc communication between at least two devices.

The present invention may be a system, a method, an apparatus and/or a computer program product at any possible technical detail level of integration. The computer program product can include a computer readable storage medium (or media) having computer readable program instructions thereon for causing a processor to carry out aspects of the present invention. The computer readable storage medium can be a tangible device that can retain and store instructions for use by an instruction execution device. The computer readable storage medium can be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium can also include the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network can comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device. Computer readable program instructions for carrying out operations of the present invention can be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions can execute entirely on the user's computer, partly on the user's computer, as a standalone software package, partly on the user's computer and partly on a remote computer or entirely on the remote computer or server. In the latter scenario, the remote computer can be connected to the user's computer through any type of network, including a local area network (LAN) or a wide area network (WAN), or the connection can be made to an external computer (for example, through the Internet using an Internet Service Provider). In some embodiments, electronic circuitry including, for example, programmable logic circuitry, field-programmable gate arrays (FPGA), or programmable logic arrays (PLA) can execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions. These computer readable program instructions can be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions can also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks. The computer readable program instructions can also be loaded onto a computer, other programmable data processing apparatus, or other device to cause a series of operational acts to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowcharts and block diagrams in the Figures illustrate the architecture, functionality, and operation of possible implementations of systems, methods, and computer program products according to various embodiments of the present invention. In this regard, each block in the flowchart or block diagrams can represent a module, segment, or portion of instructions, which comprises one or more executable instructions for implementing the specified logical function(s). In some alternative implementations, the functions noted in the blocks can occur out of the order noted in the Figures. For example, two blocks shown in succession can, in fact, be executed substantially concurrently, or the blocks can sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

While the subject matter has been described above in the general context of computer-executable instructions of a computer program product that runs on a computer and/or computers, those skilled in the art will recognize that this disclosure also can or can be implemented in combination with other program modules. Generally, program modules include routines, programs, components, data structures, etc. that perform particular tasks and/or implement particular abstract data types. Moreover, those skilled in the art will appreciate that the inventive computer-implemented methods can be practiced with other computer system configurations, including single-processor or multiprocessor computer systems, mini-computing devices, mainframe computers, as well as computers, hand-held computing devices (e.g., PDA, phone), microprocessor-based or programmable consumer or industrial electronics, and the like. The illustrated aspects can also be practiced in distributed computing environments in which tasks are performed by remote processing devices that are linked through a communications network. However, some, if not all aspects of this disclosure can be practiced on stand-alone computers. In a distributed computing environment, program modules can be located in both local and remote memory storage devices.

As used in this application, the terms "component," "system," "platform," "interface," and the like, can refer to and/or can include a computer-related entity or an entity related to an operational machine with one or more specific functionalities. The entities disclosed herein can be either hardware, a combination of hardware and software, software, or software in execution. For example, a component can be, but is not limited to being, a process running on a processor, a processor, an object, an executable, a thread of execution, a program, and/or a computer. By way of illustration, both an application running on a server and the server can be a component. One or more components can reside within a process and/or thread of execution and a component can be localized on one computer and/or distributed between two or more computers. In another example, respective components can execute from various computer readable media having various data structures stored thereon. The components can communicate via local and/or remote processes such as in accordance with a signal having one or more data packets (e.g., data from one component interacting with another component in a local system, distributed system, and/or across a network such as the Internet with other systems via the signal). As another example, a component can be an apparatus with specific functionality provided by mechanical parts operated by electric or electronic circuitry, which is operated by a software or firmware application executed by a processor. In such a case, the processor can be internal or external to the apparatus and can execute at least a part of the software or firmware application. As yet another example, a component can be an apparatus that provides specific functionality through electronic components without mechanical parts, wherein the electronic components can include a processor or other means to execute software or firmware that confers at least in part the functionality of the electronic components. In an aspect, a component can emulate an electronic component via a virtual machine, e.g., within a cloud computing system.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form. As used herein, the terms "example" and/or "exemplary" are utilized to mean serving as an example, instance, or illustration. For the avoidance of doubt, the subject matter disclosed herein is not limited by such examples. In addition, any aspect or design described herein as an "example" and/or "exemplary" is not necessarily to be construed as preferred or advantageous over other aspects or designs, nor is it meant to preclude equivalent exemplary structures and techniques known to those of ordinary skill in the art.

As it is employed in the subject specification, the term "processor" can refer to substantially any computing processing unit or device comprising, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Further, processors can exploit nano-scale architectures such as, but not limited to, molecular and quantum-dot based transistors, switches and gates, in order to optimize space usage or enhance performance of user equipment. A processor can also be implemented as a combination of computing processing units. In this disclosure, terms such as "store," "storage," "data store," data storage," "database," and substantially any other information storage component relevant to operation and functionality of a component are utilized to refer to "memory components," entities embodied in a "memory," or components comprising a memory. It is to be appreciated that memory and/or memory components described herein can be either volatile memory or nonvolatile memory, or can include both volatile and nonvolatile memory. By way of illustration, and not limitation, nonvolatile memory can include read only memory (ROM), programmable ROM (PROM), electrically programmable ROM (EPROM), electrically erasable ROM (EEPROM), flash memory, or nonvolatile random access memory (RAM) (e.g., ferroelectric RAM (FeRAM). Volatile memory can include RAM, which can act as external cache memory, for example. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM (RDRAM). Additionally, the disclosed memory components of systems or computer-implemented methods herein are intended to include, without being limited to including, these and any other suitable types of memory.

What has been described above include mere examples of systems and computer-implemented methods. It is, of course, not possible to describe every conceivable combination of components or computer-implemented methods for purposes of describing this disclosure, but one of ordinary skill in the art can recognize that many further combinations and permutations of this disclosure are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim.

The descriptions of the various embodiments have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A system, comprising:
a memory that stores computer-executable components; and
a processor, operably coupled to the memory, that executes the computer-executable components stored in the memory, wherein the processor;
obtains a computational quantum algorithm that models properties of the molecule, wherein the computational quantum algorithm is employable for simulating the molecule at a defined precision using a first number of qubits of a quantum device;
identifies a spatial point group symmetry operation associated with the molecule;
generates a unitary matrix that corresponds to the spatial point group symmetry operation;
generates a Hermitian matrix based on the unitary matrix;
generates a diagonalized second quantization representation of the spatial point group symmetry operation based on the Hermitian matrix converts the diagonalized second quantization representation into a single Pauli string;
tapers the computational quantum algorithm based on the single Pauli string, wherein the tapered computational quantum algorithm is employable for simulating the molecule at the defined precision using a second number of qubits of the quantum device that is less than the first number of qubits; and
simulates, using the tapered computational quantum algorithm with the second number of qubits of the quantum device, the molecule.

2. The system of claim 1, wherein the processor converts the diagonalized second quantization representation by one from a group consisting of a Jordan-Wigner transformation, a Parity transformation, a Bravyi-Kitaev transformation, a Superfast Encoding transformation, and a Generalized Superfast Encoding transformation.

3. The system of claim 1, wherein:
the molecule is one from a group consisting of hydrogen ($H_2$), hydrogen chloride (HCl), beryllium hydride ($BeH_2$), ammonia ($NH_3$), water ($H_2O$), ethylene ($C_2H_4$), boron trifluoride ($BF_3$), lithium hydride (LiH), carbon dioxide ($CO_2$), and acetylene ($C_2H_2$).

4. The system of claim 1, wherein:
the spatial point group symmetry operation is one from a group consisting of a proper rotation about a principal axis, a reflection through a plane of symmetry, an inversion about a center of symmetry, and an improper rotation about the principal axis.

5. The system of claim 1, wherein:
the generating the unitary matrix comprises generating a unitary n-by-n permutation matrix, R, that corresponds to the spatial point group symmetry operation, such that there exists a first matrix, $\hat{R}$, wherein $\hat{R}a_p\hat{R}^\dagger=\Sigma_{q=1}^n \langle p|R|q\rangle a_q$ for all $1\leq p\leq n$, wherein n is a number of fermionic modes of the molecule, and wherein $a_p$ and $a_q$ are fermionic annihilation operators;
the generating the Hermitian matrix comprises generating the Hermitian matrix, G, wherein R=exp (iG) such that there exists a second matrix, $\hat{G}$, wherein $\hat{R}=\exp(i\hat{G})$, such that there exists a second matrix, $\hat{G}$, wherein $\hat{G}=\Sigma_{p,q=1}^n \langle p|G|q\rangle a_p^\dagger a_q$; and
the generating the diagonalized second quantization representation comprises:
generating a unitary n-by-n matrix, V, that diagonalizes G such that $V^\dagger GV=\Sigma_{p=1}^n \lambda_p |p\rangle\langle p|$, wherein $\lambda_p$ is a real eigenvalue, such that there exists a third matrix, $\hat{V}$, wherein $\hat{V}$, wherein $\hat{V}a_p\hat{V}^\dagger=\Sigma_{q=1}^n \langle p|V|q\rangle a_q$ for all $1\leq p\leq n$; and
generating as the diagonalized second quantization representation an operator S such that $S=\hat{V}\hat{R}\hat{V}^\dagger=\exp(\hat{V}\hat{G}\hat{V}^\dagger)=\Pi_{p=1}^n \exp(i\lambda_p a_p^\dagger a_p)$.

6. The system of claim 5, wherein:
$R^2=I$, wherein I is an identity matrix, such that $\lambda_p \in \{0,\pi\}$, and such that $S=\Pi_{p\in M}(-1)^{a_p^\dagger a_p}$ wherein M is a subset of fermionic modes having $\lambda_p=\pi$.

7. The system of claim 6, wherein the processor converts the operator S into a single Pauli-Z string via a Jordan-Wigner transformation, such that $S=\Pi_{p\in M}\sigma_z^p$, wherein $\sigma_z$ is a Pauli-Z matrix.

8. A computer-implemented method, comprising:
obtaining, by a system operatively coupled to a processor, a computational quantum algorithm that models properties of the molecule, wherein the computational quantum algorithm is employable for simulating the molecule at a defined precision using a first number of qubits of a quantum device;

identifying, by the system, a spatial point group symmetry operation associated with the molecule;

generating, by the system, a unitary matrix that corresponds to the spatial point group symmetry operation;

generating, by the system, a Hermitian matrix based on the unitary matrix;

generating, by a system operatively coupled to a processor, a diagonalized second quantization representation of the spatial point group symmetry operation based on the Hermitian matrix;

converting, by the system, the diagonalized second quantization representation into a single Pauli string; and tapering off, by the system, the computational quantum algorithm based on the single Pauli string, wherein the tapered computational quantum algorithm is employable for simulating the molecule at the defined precision using a second number of qubits of the quantum device that is less than the first number of qubits; and simulating, by the system, using the tapered computational quantum algorithm with the second number of qubits of the quantum device, the molecule.

9. The computer-implemented method of claim 8, wherein:
the converting the diagonalized second quantization representation includes comprises employing one from a group consisting of a Jordan-Wigner transformation, a Parity transformation, a Bravyi-Kitaev transformation, a Superfast Encoding transformation, and a Generalized Superfast Encoding transformation.

10. The computer-implemented method of claim 8, wherein:
the molecule is one from a group consisting of hydrogen ($H_2$), hydrogen chloride (HCl), beryllium hydride ($BeH_2$), ammonia ($NH_3$), water ($H_2O$), ethylene ($C_2H_4$), boron trifluoride ($BF_3$), lithium hydride (LiH), carbon dioxide ($CO_2$), and acetylene ($C_2H_2$).

11. The computer-implemented method of claim 8, wherein:
the spatial point group symmetry operation is one from a group consisting of a proper rotation about a principal axis, a reflection through a plane of symmetry, an inversion about a center of symmetry, and an improper rotation about the principal axis.

12. The computer-implemented method of claim 8, wherein:
the generating the unitary matrix comprises generating a unitary n-by-n permutation matrix, R, that corresponds to the spatial point group symmetry operation, such that there exists a first matrix, $\hat{R}$, wherein $\hat{R}a_p\hat{R}^\dagger = \Sigma_{q=1}^n \langle p|R|q \rangle a_q$ for all $1 \leq p \leq n$, wherein n is a number of fermionic modes of the molecule, and wherein $a_p$ and $a_q$ are fermionic annihilation operators;

the generating the Hermitian matrix comprises generating the Hermitian matrix, G, wherein R=exp (iG) such that there exists a second matrix, $\hat{G}$, wherein R=exp(iG), such that there exists a second matrix, $\hat{G}$, wherein $\hat{G}=\Sigma_{p,q=1}^n \langle p|G|q \rangle a_p^\dagger a_q$; and the generating the diagonalized second quantization representation comprises:
generating a unitary n-by-n matrix, V, that diagonalizes G such that $V^\dagger GV = \Sigma_{p=1}^n \lambda_p |p\rangle\langle p|$, wherein $\lambda_p$ is a real eigenvalue, such that there exists a third matrix, $\hat{V}$, wherein $\hat{V}a_p\hat{V}^\dagger = \Sigma_{q=1}^n \langle p|V|q \rangle a_q$ for all $1 \leq p \leq n$; and generating as the diagonalized second quantization representation an operator S such that $S=\hat{V}\hat{R}\hat{V}^\dagger=\exp(\hat{V}\hat{G}\hat{V}^\dagger)=\Pi_{p=1}^n \exp(i\lambda_p a_p^\dagger a_p)$.

13. The computer-implemented method of claim 12, wherein:
$R^2=I$, wherein I is an identity matrix, such that $\lambda_p \in \{0, \pi\}$, and such that $S=\Pi_{p \in M}(-1)^{a_p^\dagger a_p}$ wherein M is a subset of fermionic modes having $\lambda_p=\pi$.

14. The computer-implemented method of claim 13, wherein:
the converting the operator S into a single Pauli-Z string comprises employing a Jordan-Wigner transformation such that $S=\Pi_{p \in M}\sigma_z^p$, wherein $\sigma_z$ is a Pauli-Z matrix.

15. A computer program product for facilitating precision-preserving qubit reduction based on spatial symmetries of fermionic systems, the computer program product comprising a non-transitory computer readable medium having program instructions embodied therewith, the program instructions executable by a processing component to cause the processing component to:

obtain a computational quantum algorithm that models properties of the molecule, wherein the computational quantum algorithm is employable for simulating the molecule at a defined precision using a first number of qubits of a quantum device;

identify a spatial point group symmetry operation associated with the molecule;

generate a unitary matrix that corresponds to the spatial point group symmetry operation;

generate a Hermitian matrix based on the unitary matrix;

generate a diagonalized second quantization representation of the spatial point group symmetry operation based on the Hermitian matrix;

convert the diagonalized second quantization representation into a single Pauli string; and taper the computational quantum algorithm based on the single Pauli string, wherein the tapered computational quantum algorithm is employable for simulating the molecule at the defined precision using a second number of qubits of the quantum device that is less than the first number of qubits; and simulate, using the tapered computational quantum algorithm with the second number of qubits of the quantum device, the molecule.

16. The computer program product of claim 15, wherein:
the program instructions are further executable to cause the processing component to convert the diagonalized second quantization representation via one from a group consisting of a Jordan-Wigner transformation, a Parity transformation, a Bravyi-Kitaev transformation, a Superfast Encoding transformation, and a Generalized Superfast Encoding transformation.

17. The computer program product of claim 15, wherein:
the molecule is one from a group consisting of hydrogen ($H_2$), hydrogen chloride (HCl), beryllium hydride ($BeH_2$), ammonia ($NH_3$), water ($H_2O$), ethylene ($C_2H_4$), boron trifluoride ($BF_3$), lithium hydride (LiH), carbon dioxide ($CO_2$), and acetylene ($C_2H_2$).

18. The computer program product of claim 15, wherein:
the generating the unitary matrix comprises generating a unitary n-by-n permutation matrix, R, that corresponds to the spatial point group symmetry operation, such that there exists a first matrix, $\hat{R}$, wherein $\hat{R}a_p\hat{R}^\dagger = \Sigma_{q=1}^n \langle p|R|q \rangle a_q$ for all $1 \leq p \leq n$, wherein n is a number of fermionic modes of the molecule, and wherein $a_p$ and $a_q$ are fermionic annihilation operators;

the generating the Hermitian matrix comprises generating the Hermitian matrix, G, wherein R=exp (iG) such that there exists a second matrix, $\hat{G}$, wherein R=exp(iG), such that there exists a second matrix, $\hat{G}$, wherein $\hat{G}=\Sigma_{p,q=1}^{n} \langle p|G|q\rangle a_p^\dagger a_q$; and the generating the diagonalized second quantization representation comprises:

generating a unitary n-by-n matrix, V, that diagonalizes G such that $V^\dagger GV = \Sigma_{p=1}^{n} \lambda_p |\rangle\langle p|$, wherein $\lambda_p$ is a real eigenvalue, such that there exists a third matrix, $\hat{V}$, wherein $\hat{V}$, wherein $\hat{V} a_p \hat{V}^\dagger = \Sigma_{q=1}^{n} \langle p|V|q\rangle a_q$ for all $1 \leq p \leq n$; and generating as the diagonalized second quantization representation an operator S such that $S=\hat{V}\hat{R}\hat{V}^\dagger = \exp(\hat{V}\hat{G}\hat{V}^\dagger) = \Pi_{p=1}^{n} \exp(i\lambda_p a_p^\dagger a_p)$.

19. The computer program product of claim 18, wherein: $R^2=I$, wherein I is an identity matrix, such that $\lambda_p \in \{0, \pi\}$, and such that $S=\Pi_{p\in M}(-1)^{a_p^\dagger a_p}$ wherein M is a subset of fermionic modes having $\lambda_p=\pi$.

20. The computer program product of claim 19, wherein: the program instructions are further executable to cause the processing component to convert the operator S into a single Pauli-Z string via a Jordan-Wigner transformation such that $S=\Pi_{p\in M}\sigma_z^p$, wherein $\sigma_z$ is a Pauli-Z matrix.

\* \* \* \* \*